US010767932B2

(12) United States Patent
Noureldin et al.

(10) Patent No.: US 10,767,932 B2
(45) Date of Patent: Sep. 8, 2020

(54) RECOVERY AND RE-USE OF WASTE ENERGY IN INDUSTRIAL FACILITIES

(71) Applicant: Saudi Arabian Oil Company, Dhahran (SA)

(72) Inventors: Mahmoud Bahy Mahmoud Noureldin, Dhahran (SA); Hani Mohammed Al Saed, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/180,828

(22) Filed: Nov. 5, 2018

(65) Prior Publication Data

US 2019/0072336 A1    Mar. 7, 2019

Related U.S. Application Data

(63) Continuation of application No. 15/241,989, filed on Aug. 19, 2016, now Pat. No. 10,119,764.

(Continued)

(51) Int. Cl.
*F28D 7/00* (2006.01)
*C10G 45/02* (2006.01)
(Continued)

(52) U.S. Cl.
CPC ......... *F28D 7/0083* (2013.01); *B01D 3/007* (2013.01); *B01D 3/32* (2013.01); *B01D 51/10* (2013.01);
(Continued)

(58) Field of Classification Search
CPC ... C02F 1/586; B01D 53/047; B01D 53/1462; B01D 53/185; B01D 53/343; B01D 53/48; B01D 53/8603; B01D 53/96; B01D 51/10; B01D 3/007; B01D 3/32; C01B 3/34; F28D 7/0083; F28F 9/26; F01K 27/00;
(Continued)

(56) References Cited

U.S. PATENT DOCUMENTS 3,995,428 A    12/1976 Roberts
4,109,469 A    8/1978 Carson
(Continued)

FOREIGN PATENT DOCUMENTS

CN    1844325    10/2006
CN    101424453    5/2009
(Continued)

OTHER PUBLICATIONS

Gulf Cooperation Council Examination Report issued in GCC Application No. GC 2016-37141 dated Jul. 7, 2019, 3 pages.
(Continued)

*Primary Examiner* — Brian A McCaig
(74) *Attorney, Agent, or Firm* — Fish & Richardson P.C.

(57) ABSTRACT

Configurations and related processing schemes of direct or indirect (or both) inter-plants heating systems synthesized for grassroots medium grade crude oil semi-conversion refineries to increase energy efficiency from specific portions of low grade waste heat sources are described. Configurations and related processing schemes of direct or indirect (or both) inter-plants heating systems synthesized for integrated medium grade crude oil semi-conversion refineries and aromatics complex for increasing energy efficiency from specific portions of low grade waste sources are also described.

25 Claims, 27 Drawing Sheets

Related U.S. Application Data

(60) Provisional application No. 62/209,217, filed on Aug. 24, 2015, provisional application No. 62/209,147, filed on Aug. 24, 2015, provisional application No. 62/209,188, filed on Aug. 24, 2015, provisional application No. 62/209,223, filed on Aug. 24, 2015.

(51) Int. Cl.

| | | |
|---|---|---|
| C10G 35/04 | (2006.01) | |
| C10L 3/10 | (2006.01) | |
| C07C 7/08 | (2006.01) | |
| C10G 65/12 | (2006.01) | |
| C10G 33/06 | (2006.01) | |
| C10G 45/00 | (2006.01) | |
| C10K 3/04 | (2006.01) | |
| F01K 27/00 | (2006.01) | |
| C01B 3/34 | (2006.01) | |
| B01D 3/00 | (2006.01) | |
| B01D 3/32 | (2006.01) | |
| B01D 51/10 | (2006.01) | |
| B01D 53/047 | (2006.01) | |
| B01D 53/14 | (2006.01) | |
| B01D 53/18 | (2006.01) | |
| B01D 53/34 | (2006.01) | |
| B01D 53/48 | (2006.01) | |
| B01D 53/86 | (2006.01) | |
| B01D 53/96 | (2006.01) | |
| C02F 1/58 | (2006.01) | |
| C10G 45/44 | (2006.01) | |
| C10G 47/00 | (2006.01) | |
| F28F 9/26 | (2006.01) | |
| C10G 65/00 | (2006.01) | |
| F01D 17/14 | (2006.01) | |
| F01K 3/18 | (2006.01) | |
| F01K 13/02 | (2006.01) | |
| H02K 7/18 | (2006.01) | |
| C10G 69/00 | (2006.01) | |
| F01K 25/06 | (2006.01) | |
| F01K 25/08 | (2006.01) | |
| F01K 27/02 | (2006.01) | |
| F01K 13/00 | (2006.01) | |
| F01K 23/06 | (2006.01) | |
| C01B 3/24 | (2006.01) | |
| C02F 101/10 | (2006.01) | |
| C02F 101/16 | (2006.01) | |
| C02F 103/18 | (2006.01) | |
| C02F 103/36 | (2006.01) | |

(52) U.S. Cl.
CPC ....... *B01D 53/047* (2013.01); *B01D 53/1462* (2013.01); *B01D 53/185* (2013.01); *B01D 53/343* (2013.01); *B01D 53/48* (2013.01); *B01D 53/8603* (2013.01); *B01D 53/96* (2013.01); *C01B 3/24* (2013.01); *C01B 3/34* (2013.01); *C02F 1/586* (2013.01); *C07C 7/08* (2013.01); *C10G 33/06* (2013.01); *C10G 35/04* (2013.01); *C10G 45/00* (2013.01); *C10G 45/02* (2013.01); *C10G 45/44* (2013.01); *C10G 47/00* (2013.01); *C10G 65/00* (2013.01); *C10G 65/12* (2013.01); *C10G 69/00* (2013.01); *C10K 3/04* (2013.01); *C10L 3/101* (2013.01); *C10L 3/103* (2013.01); *C10L 3/104* (2013.01); *F01D 17/145* (2013.01); *F01K 3/185* (2013.01); *F01K 13/00* (2013.01); *F01K 13/02* (2013.01); *F01K 23/06* (2013.01); *F01K 23/064* (2013.01); *F01K 25/06* (2013.01); *F01K 25/08* (2013.01); *F01K 27/00* (2013.01); *F01K 27/02* (2013.01); *F28F 9/26* (2013.01); *H02K 7/1823* (2013.01); *B01D 2252/204* (2013.01); *C01B 2203/0227* (2013.01); *C01B 2203/0233* (2013.01); *C01B 2203/0283* (2013.01); *C01B 2203/043* (2013.01); *C01B 2203/127* (2013.01); *C02F 2101/10* (2013.01); *C02F 2101/101* (2013.01); *C02F 2101/16* (2013.01); *C02F 2103/18* (2013.01); *C02F 2103/36* (2013.01); *C10G 2300/202* (2013.01); *C10G 2300/207* (2013.01); *C10G 2300/4006* (2013.01); *C10G 2300/4056* (2013.01); *C10G 2400/04* (2013.01); *C10G 2400/30* (2013.01); *C10L 2290/06* (2013.01); *C10L 2290/541* (2013.01); *Y02P 20/129* (2015.11); *Y02P 30/10* (2015.11)

(58) Field of Classification Search
CPC ........ C10G 45/00; C10G 45/44; C10G 47/00; C10G 65/00; C10K 3/04
See application file for complete search history.

(56) References Cited

U.S. PATENT DOCUMENTS

| | | |
|---|---|---|
| 4,291,232 A | 9/1981 | Cardone |
| 4,471,619 A | 9/1984 | Nolley, Jr. |
| 4,512,155 A | 4/1985 | Sheinbaum |
| 4,792,390 A | 12/1988 | Staggs |
| 4,962,238 A | 10/1990 | Wolfe |
| 5,007,240 A | 4/1991 | Ishida |
| 5,164,070 A | 11/1992 | Munro |
| 5,240,476 A | 8/1993 | Hegarty |
| 5,497,624 A | 3/1996 | Amir |
| 6,733,636 B1 | 5/2004 | Heins |
| 8,046,999 B2 | 11/2011 | Doty |
| 9,328,634 B2 | 5/2016 | Ikegami |
| 9,562,201 B2 | 2/2017 | Noureldin |
| 9,851,153 B2 | 12/2017 | Noureldin |
| 2002/0023538 A1 | 2/2002 | Agarwal |
| 2003/0092952 A1 | 5/2003 | Netzer |
| 2003/0132138 A1 | 7/2003 | Mehra |
| 2004/0088993 A1 | 5/2004 | Radcliff et al. |
| 2004/0186332 A1 | 9/2004 | Kong |
| 2006/0010872 A1 | 1/2006 | Singh |
| 2008/0128134 A1 | 6/2008 | Mudunuri |
| 2008/0174115 A1 | 7/2008 | Lambirth |
| 2008/0257413 A1 | 10/2008 | Noureldin et al. |
| 2008/0289588 A1 | 11/2008 | Wees et al. |
| 2008/0314726 A1 | 12/2008 | Choros |
| 2009/0000299 A1 | 1/2009 | Ast |
| 2009/0000906 A1 | 1/2009 | Petri |
| 2009/0071652 A1 | 3/2009 | Vinegar |
| 2009/0225929 A1 | 9/2009 | Genta et al. |
| 2009/0287029 A1 | 11/2009 | Anumakonda et al. |
| 2009/0301087 A1 | 12/2009 | Borissov et al. |
| 2010/0146974 A1 | 6/2010 | Ast |
| 2010/0242476 A1 | 9/2010 | Ast |
| 2010/0263380 A1 | 10/2010 | Biederman |
| 2010/0319346 A1 | 12/2010 | Ast |
| 2010/0326076 A1 | 12/2010 | Ast |
| 2011/0016863 A1 | 1/2011 | Ernst |
| 2011/0072819 A1 | 3/2011 | Silva |
| 2011/0072820 A1 | 3/2011 | Finkenrath |
| 2011/0083437 A1 | 4/2011 | Ast |
| 2011/0158858 A1 | 6/2011 | Alves |
| 2012/0031096 A1 | 2/2012 | Acikgoz et al. |
| 2012/0047889 A1 | 3/2012 | Acikgoz et al. |
| 2012/0048718 A1 | 3/2012 | Werba |
| 2012/0085096 A1 | 4/2012 | Penton et al. |
| 2012/0131921 A1 | 5/2012 | Held |
| 2012/0273204 A1 | 11/2012 | De Francesco |
| 2012/0279728 A1 | 11/2012 | Northrop |
| 2012/0279900 A1 | 11/2012 | Noureldin et al. |

(56) References Cited

U.S. PATENT DOCUMENTS

| | | | |
|---|---|---|---|
| 2012/0285169 | A1 | 11/2012 | Freund |
| 2012/0298552 | A1 | 11/2012 | Koseoglu |
| 2013/0104546 | A1 | 5/2013 | Goswami |
| 2013/0145763 | A1 | 6/2013 | Mirmobin et al. |
| 2013/0165534 | A1 | 6/2013 | McComish |
| 2013/0213040 | A1 | 8/2013 | Goswami |
| 2013/0231909 | A1 | 9/2013 | Noureldin |
| 2013/0238154 | A1 | 9/2013 | Noureldin |
| 2013/0334060 | A1 | 12/2013 | Koseoglu et al. |
| 2014/0090405 | A1 | 4/2014 | Held et al. |
| 2014/0142364 | A1 | 5/2014 | Io |
| 2014/0260311 | A1 | 9/2014 | Berlowitz |
| 2015/0050741 | A1 | 2/2015 | Tour et al. |
| 2015/0159079 | A1 | 6/2015 | Huh et al. |
| 2015/0252692 | A1 | 9/2015 | Honkatukia et al. |
| 2015/0377079 | A1 | 12/2015 | Noureldin |
| 2016/0045841 | A1 | 2/2016 | Kaplan |
| 2017/0082373 | A1 | 3/2017 | Noureldin et al. |

FOREIGN PATENT DOCUMENTS

| | | |
|---|---|---|
| CN | 102027096 | 4/2011 |
| CN | 102371108 | 3/2012 |
| CN | 102796558 | 11/2012 |
| CN | 102947423 | 2/2013 |
| CN | 203928084 | 11/2014 |
| CN | 104560082 | 4/2015 |
| CN | 104619959 | 5/2015 |
| CN | 107364424 | 11/2017 |
| DE | 3731978 | 3/1988 |
| EP | 292391 | 11/1988 |
| EP | 949318 | 10/1999 |
| EP | 2516326 | 10/2012 |
| FR | 2990990 | 11/2013 |
| SU | 295317 | 10/1977 |
| WO | 97/21786 | 6/1997 |
| WO | 2004102082 | 11/2004 |
| WO | 2011090553 | 7/2011 |
| WO | 2012048132 | 4/2012 |
| WO | 2012158478 | 11/2012 |
| WO | 2013055864 | 4/2013 |
| WO | 2014205163 | 12/2014 |
| WO | WO 2015006872 | 1/2015 |

OTHER PUBLICATIONS

Gulf Cooperation Council Examination Report issued in GCC Application No. GC 2016-37123 dated Jul. 7, 2019, 3 pages.
Communication Pursuant to Article 94(3) EPC issued in European Application No. 16758061.2 dated Dec. 18, 2018, 4 pages.
Communication Pursuant to Article 94(3) EPC issued in European Application No. 16758058.8 dated Dec. 11, 2018, 4 pages.
CN Office Action in Chinese Appln. No. 201680061070.5, dated Aug. 27, 2019, 11 pages (with English translation).
European Office Action in European Application No. 16758061.2-1101, dated Aug. 20, 2019. 6 pages.
Oluleye et al, "Evaluating the potential of process sites for waste heat recovery", Applied Energy., vol. 161, Jul. 23, 2015, pp. 627-646.
Communication Pursuant to Article 94(3) EPC issued in European Application No. 16758061.2 dated May 28, 2019, 5 pages.
Communication Pursuant to Article 94(3) issued in European Application No. 16758058.8 dated Apr. 18, 2019, 4 pages.
D. Ayou, J. C. Bruno, R. Saravanan and A. Coronas, "An Overview of Combined Absorption Power and Cooling Cycles," Renewable sustainable energy reviews, 21 (2013), 728-748.
D. Zheng, B. Chen, Y. Qi and H. Jin, "Thermodynamic analysis of a novel absorption power/cooling combined cycle," Applied Energy, 83 (2006), 311-323.
Feng Xu, D. Yogi Goswami and Sunil S. Bhagwat, "A combined power/cooling cycle," Energy, 25 (2000), 233-246.

Gary, "Petroleum Refining Technology and Economics: Figure 1.1 Refinery Flow Diagram," CRC Press, 5th ed., 2007, p. 3.
Hasan et al., "First and Second Law Analysis of a New Power and Refrigeration Thermodynamic Cycle using a Solar Heat Source," Pergamon, Solar Energy, vol. 73, No. 5, Nov. 1, 2002, pp. 385-393.
J. Hua, Y. Chen, Y. Wang and A.P. Roskilly, "Thermodynamic analysis of ammonia-water power/chilling cogeneration cycle with low grade waste heat," Applied thermal engineering, 64 (2014), 483-490.
J. Wang, Y. Dai and L. Gao, "Parametric analysis and optimization for a combined power and refrigeration cycle," Applied Energy, 85 (2008), 1071-1085.
Marcilly, "Acido-Basic Catalysis: Applications to refining and Petrochemistry," IFP Publications, 2005, pp. 512-513.
Meng Liu, and Na Zhang, "Proposal and analysis of a novel ammonia-water cycle for power and refrigeration cogeneration," Energy, 32 (2007), 961-970.
R.V. Padilla, G. Demirkaya, D. Yogi Goswami, E. Stefanakos, and M. A. Rahman, "Analysis of power and cooling cogeneration using ammonia-water mixture," Energy, 35 (2010), 4649-4657.
Sadrameli et al., "Optimum Operating Conditions for a Combined Power and Cooling Thermodynamic Cycle," Science Direct, Applied Energy, vol. 84, No. 3, Nov. 10, 2006, pp. 254-265.
Schaschke, "A Dictionary of Chemical Engineering: Tatoray Process," Oxford, 2014, p. 371.
STECCO, "Kalina Cycles: Some Possible Applications and Comments," Proceedings of the American Power Conference, XP000609703, Jan. 1, 1993, vol. 1, pp. 196-201.
Tamm et al., "Theoretical and Experimental Investigation of an Ammonia-Water Power and Refrigeration Thermodynamic Cycle," Science Direct, Solar Energy, vol. 76, No. 1-3, Jan. 1, 2004, pp. 217-228.
Vidal, "Analysis of a Combined Power and Refrigeration Cycle by the Exergy Method," Science Direct, Energy 31, Dec. 1, 2006, pp. 3401-3414.
PCT International Search Report and Written Opinion of the International Searching Authority, PCT/US2016/027417, dated Jul. 6, 2016, 11 pages.
PCT International Search Report and Written Opinion of the International Searching Authority, PCT/US2016/027797, dated Oct. 19, 2016, 12 pages.
PCT International Search Report and Written Opinion of the International Searching Authority, PCT/US2016/027794, dated Oct. 19, 2016, 13 pages.
PCT International Search Report and Written Opinion of the International Searching Authority, PCT/US2016/030063, dated Oct. 19, 2016, 13 pages.
PCT International Search Report and Written Opinion of the International Searching Authority, PCT/US2016/030156, dated Oct. 19, 2016, 12 pages.
PCT International Search Report and Written Opinion of the International Searching Authority, PCT/US2016/048074, dated Nov. 9, 2016, 12 pages.
PCT International Search Report and Written Opinion of the International Searching Authority, PCT/US2016/048042, dated Nov. 9, 2016, 12 pages.
PCT International Search Report and Written Opinion of the International Searching Authority, PCT/US2016/048067, dated Nov. 15, 2016, 11 pages.
PCT International Search Report and Written Opinion of the International Searching Authority, PCT/US2016/048066, dated Nov. 15, 2016, 11 pages.
PCT International Search Report and Written Opinion of the International Searching Authority, PCT/US2016/048078, dated Nov. 15, 2016, 12 pages.
PCT International Search Report and Written Opinion of the International Searching Authority, PCT/US2016/048076, dated Nov. 15, 2016, 12 pages.
PCT International Search Report and Written Opinion of the International Searching Authority, PCT/US2016/048207, dated Nov. 21, 2016, 12 pages.

(56) References Cited

OTHER PUBLICATIONS

PCT International Search Report and Written Opinion of the International Searching Authority, PCT/US2016/048219, dated Nov. 21, 2016, 13 pages.
PCT International Search Report and Written Opinion of the International Searching Authority, PCT/US2016/048229, dated Nov. 21, 2016, 13 pages.
PCT International Search Report and Written Opinion of the International Searching Authority, PCT/US2016/048236, dated Nov. 21, 2016, 13 pages.
PCT International Search Report and Written Opinion of the International Searching Authority, PCT/US2016/027413, dated Nov. 22, 2016, 11 pages.
PCT International Search Report and Written Opinion of the International Searching Authority, PCT/US2016/048063, dated Nov. 23, 2016, 11 pages.
PCT International Search Report and Written Opinion of the International Searching Authority, PCT/US2016/048071, dated Nov. 23, 2016, 11 pages.
PCT International Search Report and Written Opinion of the International Searching Authority, PCT/US2016/048210, dated Dec. 22, 2016, 11 pages.
PCT International Search Report and Written Opinion of the International Searching Authority, PCT/US2016/048224, dated Dec. 22, 2016, 11 pages.
PCT International Search Report and Written Opinion of the International Searching Authority, PCT/US2016/048209, dated Dec. 22, 2016, 11 pages.
PCT International Search Report and Written Opinion of the International Searching Authority, PCT/US2016/048237, dated Dec. 22, 2016, 11 pages.
PCT International Search Report and Written Opinion of the International Searching Authority, PCT/US2016/048223, dated Dec. 22, 2016, 11 pages.
PCT International Search Report and Written Opinion of the International Searching Authority, PCT/US2016/048212, dated Dec. 22, 2016, 11 pages.
CN Office Action in Chinese Appln. No. 2016800610692, dated Sep. 9, 2019, 20 pages (with English translation).
Zhang et al, "Total Site Optimization Strategy of Energy System and Application for Petrochemical Industry," Computer and Applied Chemistry, vol. 26, No. 4, pp. 339-402, Apr. 28, 2009, English Abstract 4 pages.
Gulf Cooperation Council Examination Report issued in GCC Application No. GC 2016-31901 dated Nov. 13, 2018, 3 pages.
Gulf Cooperation Council Examination Report issued in GCC Application No. GC 2016-31905 dated Nov. 13, 2018, 3 pages.
Gulf Cooperation Council Examination Report issued in GCC Application No. GC 2016-31902 dated Nov. 13, 2018, 3 pages.
Gulf Cooperation Council Examination Report issued in GCC Application No. GC 2016-31903 dated Nov. 13, 2018, 3 pages.
Chinese Office Action issued in Chinese Application No. 201680060979.9 dated Oct. 28, 2019, 10 pages (with English translation).
Chinese Office Action issued in Chinese Application No. 201680059774.9 dated Oct. 28, 2019, 10 pages (with English translation).
Indian Office Action issued in Indian Application No. 201817009037 dated Mar. 17, 2020, 6 pages.
Communication Pursuant to Article 94(3) EPC issued in European Application No. 16758058.8 dated Dec. 11, 2019, 4 pages.
Communication Pursuant to Article 94(3) EPC issued in European Application No. 16758061.2 dated Dec. 10, 2019, 4 pages.
Gulf Cooperation Council Examination Report issued in GCC Application No. GC 2016-38077 dated Dec. 16, 2019, 4 pages.
Chinese Office Action issued in Chinese Application No. 201680061070.5 dated Mar. 12, 2020, 6 pages (with English translation).

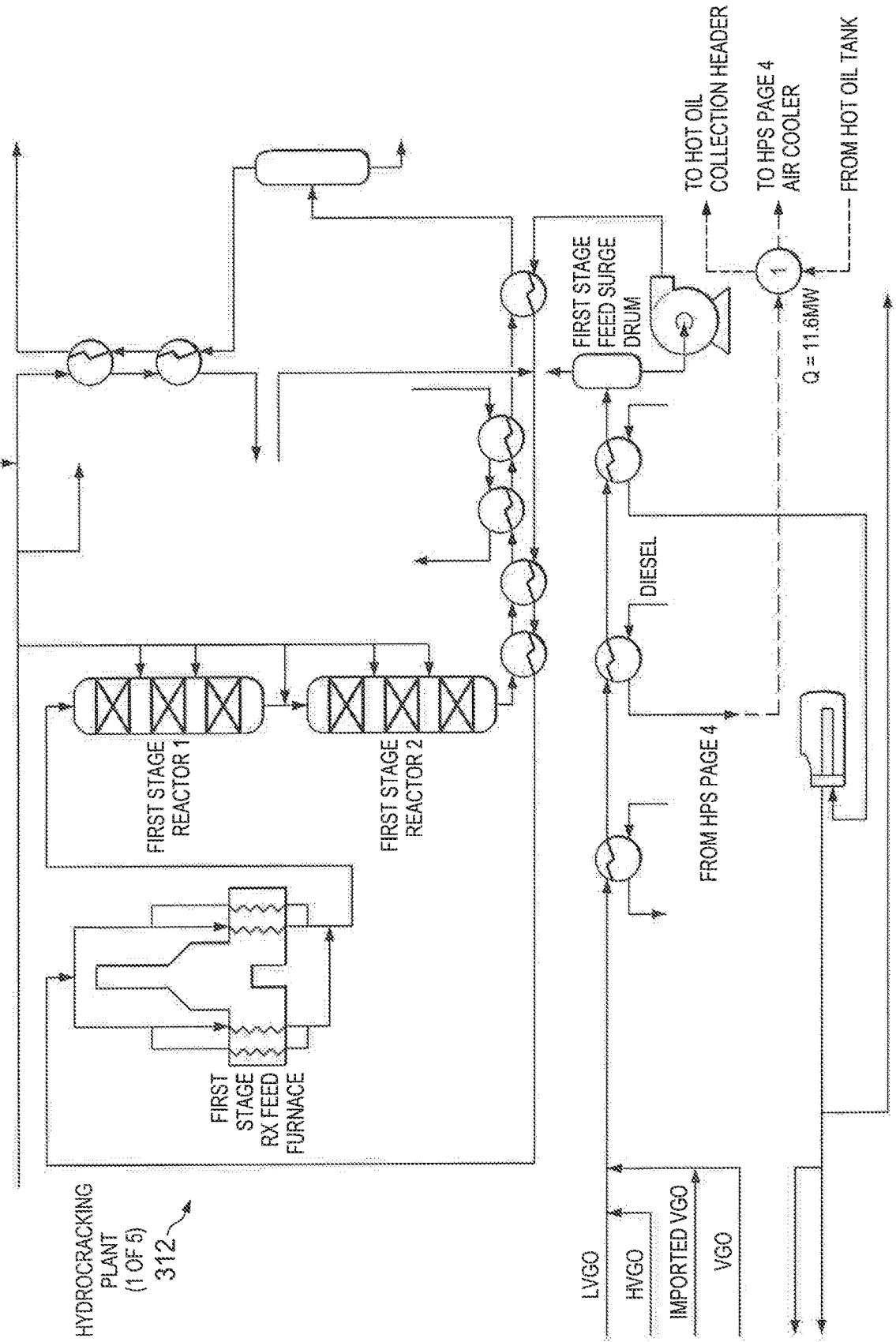
FIG. 1A (CONFIGURATION #1)

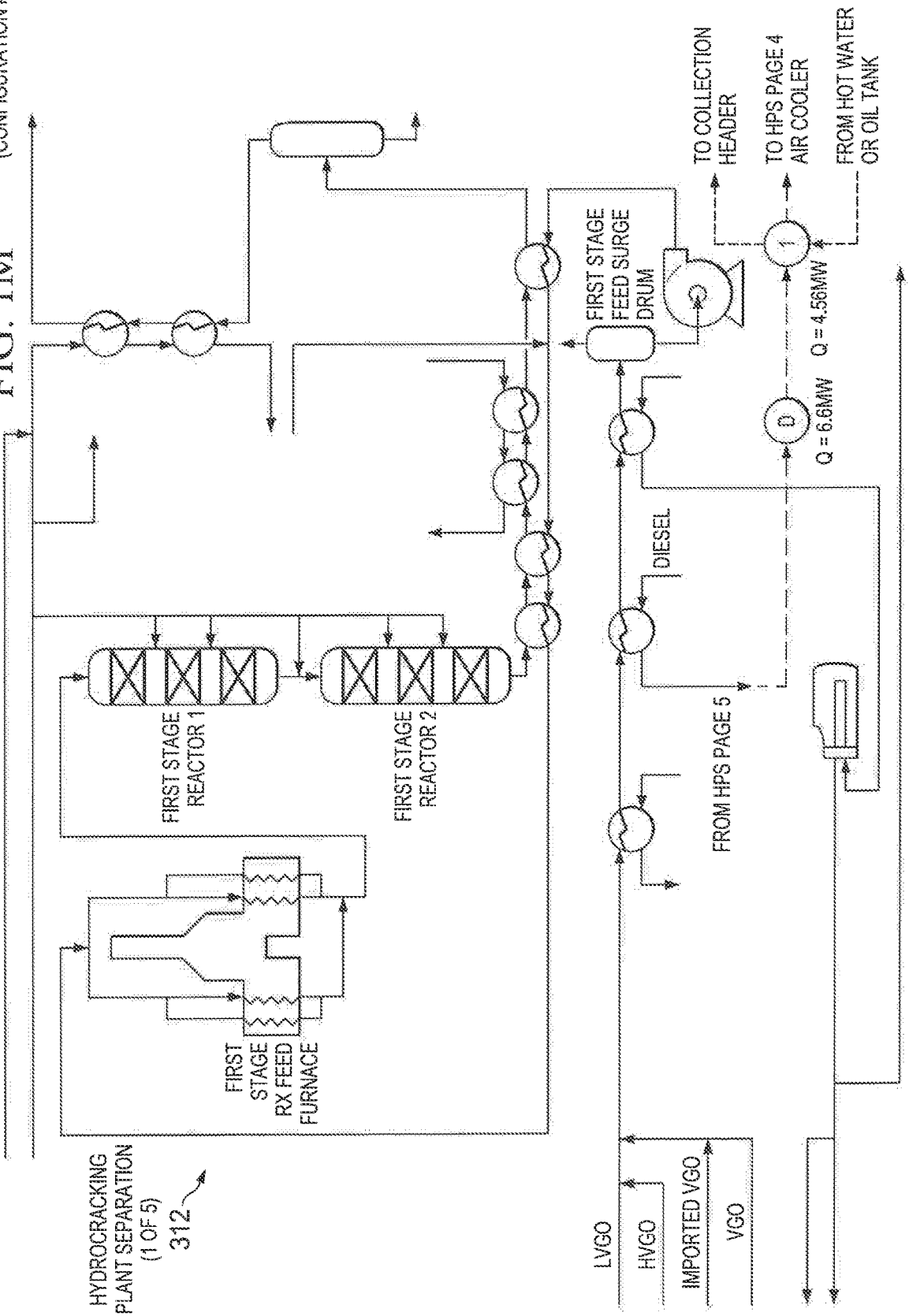
FIG. 1M (CONFIGURATION #2)

RECOVERY AND RE-USE OF WASTE ENERGY IN INDUSTRIAL FACILITIES

CROSS-REFERENCE TO RELATED APPLICATIONS

This application is a continuation application of, and claims the benefit of priority under 35 U.S.C. § 120, to U.S. patent application Ser. No. 15/241,989, filed on Aug. 19, 2016, and also claims priority under 35 U.S.C. § 119 to U.S. Provisional Patent Application Ser. No. 62/209,217, filed on Aug. 24, 2015; U.S. Provisional Patent Application Ser. No. 62/209,147, filed on Aug. 24, 2015; U.S. Provisional Patent Application Ser. No. 62/209,188, filed on Aug. 24, 2015; and U.S. Provisional Patent Application Ser. No. 62/209,223, filed on Aug. 24, 2015. The entire contents of each of the preceding applications are incorporated herein by reference in their respective entireties.

TECHNICAL FIELD

This specification relates to operating industrial facilities, for example, crude oil refining facilities or other industrial facilities that include operating plants that generate heat.

BACKGROUND

Petroleum refining processes are chemical engineering processes and other facilities used in petroleum refineries to transform crude oil into products, for example, liquefied petroleum gas (LPG), gasoline, kerosene, jet fuel, diesel oils, fuel oils, and other products. Petroleum refineries are large industrial complexes that involve many different processing units and auxiliary facilities, for example, utility units, storage tanks, and other auxiliary facilities. Each refinery can have its own unique arrangement and combination of refining processes determined, for example, by the refinery location, desired products, economic considerations, or other factors. The petroleum refining processes that are implemented to transform the crude oil into the products such as those listed earlier can generate heat, which may not be reused, and byproducts, for example, greenhouse gases (GHG), which may pollute the atmosphere. It is believed that the world's environment has been negatively affected by global warming caused, in part, due to the release of GHG into the atmosphere.

SUMMARY

This specification describes technologies relating to inter-plants waste heat recovery schemes for double digit refineries thermal energy consumption reduction from waste energy in industrial facilities.

Some aspects of the subject matter described here can be implemented as a system in a crude oil refining facility to implement the methods described here. The system can include a flow control system.

The details of one or more implementations of the subject matter described in this specification are set forth in the accompanying drawings and the description later. Other features, aspects, and advantages of the subject matter will become apparent from the description, the drawings, and the claims.

BRIEF DESCRIPTION OF THE DRAWINGS

FIGS. 1A-1L illustrate configurations and related scheme details for heating a naphtha hydro-treating plant stream, a sour water stripper plant stream, an amine regeneration plant separation section stream, a sulfur recovery plant stream and gas separation plant streams in the crude oil refining facility.

FIGS. 1M-1Y illustrate configurations and related scheme details for heating a naphtha hydro-treating plant stream, a sour water stripper plant stream, an amine regeneration plant separation section stream, a sulfur recovery plant stream and gas separation plant streams in the crude oil refining facility.

DETAILED DESCRIPTION

Figure 1B:
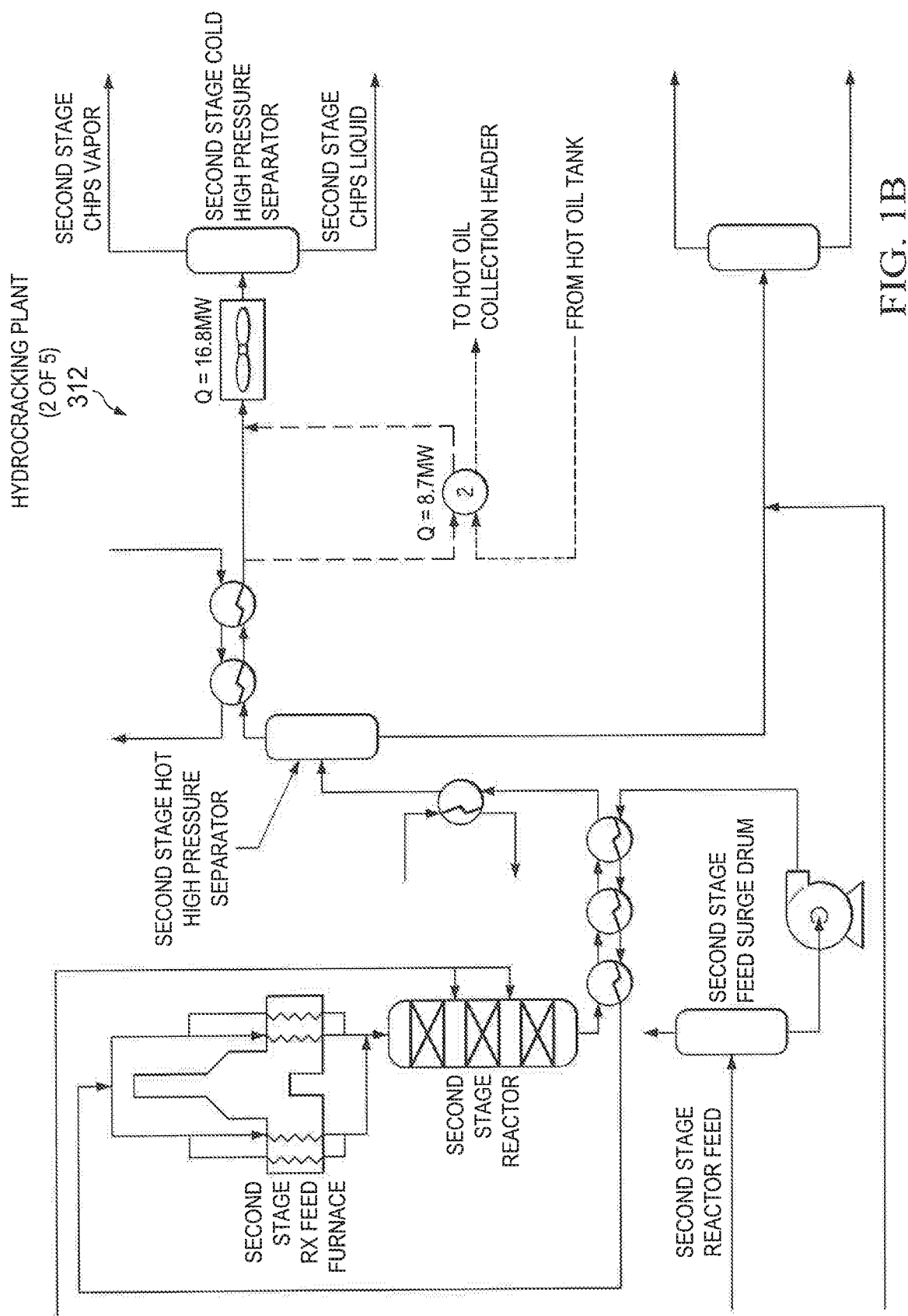

Industrial waste heat is a source for potential carbon-free power generation in many industrial facilities, for example, crude oil refineries, petrochemical and chemical complexes, and other industrial facilities. For example, a medium-size integrated crude oil refinery with aromatics up to 4,000 MM British Thermal Units per hour (Btu/hr) can be wasted to a network of air coolers extended along the crude oil and aromatics site. Some of the wasted heat can be reused to heat streams in refining sub-units of the crude oil refinery, thereby decreasing a quantity of heat that would otherwise need to be used to heat the streams. In this manner, a quantity of heat consumed by the crude oil refinery can decrease. In addition, a quantity of greenhouse gas (GHG) emission can also decrease. In some implementations, a reduction of about 34% in heating utility consumption and a reduction of about 20% in cooling utility consumption can be achieved without affecting an operational philosophy of the crude oil refinery.

The waste heat recovery and reuse techniques described here can be implemented in medium grade crude oil refining semi-conversion facilities and integrated medium grade crude oil refining semi-conversion oil refining and aromatics facilities. The implementations can result in energy efficient systems that can consume about 66% of the heating utility consumed by current state-of-the-art designs of existing and new crude oil refining facilities. The implementations can also result in decrease in pollution and in GHG emissions by about one-third relative to GHG emissions from current state-of-the-art designs of existing and new crude oil refining facilities.

In certain existing oil refining facilities, a stream in a plant (for example, a naphtha hydro-treating plant, a sour water stripper plant, or other plant) is heated using heat energy generated in a steam reboiler. In some implementations of the subject matter described here, the stream in the plant can be heated using waste heat carried by another stream in another plant (for example, a hydrocracking plant, a hydro-treating plant, a hydrogen plant, or other plant). By doing so, the heat energy generated in the steam reboiler can be decreased or eliminated. In other words, the steam reboiler need not be the only source of heat energy to heat the stream in the plant. The waste heat carried by the other stream in the other plant can either replace the heat energy generated in the steam reboiler or supplement the heat energy thereby decreasing a quantity of heat energy needed from the steam reboiler.

The subject matter described here can be implemented at different plants' specific operating modes and can be retrofitted without the need to change the network designs of existing heat exchanger designs in crude oil refineries. The minimum approach temperature used in the waste heat recovery and reuse processes can be as low as 3° C. In some implementations, higher minimum approach temperatures can be used in an initial phase at the expense of less waste heat/energy recovery, while relatively better energy saving is realized in a subsequent phase upon using the minimum approach temperature for the specific hot sources uses.

In sum, this disclosure describes several crude oil refinery-wide separation/distillation networks, configurations, and processing schemes for increasing energy efficiency of heating/cooling utilities. The increase in energy efficiency is realized by reusing all or part of waste heat, for example, low grade waste heat, carried by multiple, scattered low grade energy quality process streams.

Examples of Crude Oil Refinery Plants

1. Hydrogen Plant

Hydrogen is generally used in refineries for sulfur removal and quality improvement of hydrocarbon products. As sulfur restrictions on gasoline and diesel become stringent, the refining demand for hydrogen continues to grow. Two process schemes are employed in on-purpose hydrogen generation plants—conventional process and pressure swing adsorption (PSA) based process. Hydrogen production can include hydro-desulfurization, steam reforming, shift conversion and purification. The conventional process produces a medium-purity hydrogen, whereas the PSA-based process recovers and purifies the hydrogen to high purities, for example, purities greater than 99.9%.

2. Aromatics Complex

A typical aromatics complex includes a combination of process units for the production of basic petrochemical intermediates of benzene, toluene and xylenes (BTX) using the catalytic reforming of naphtha using continuous catalytic reformer (CCR) technology.

3. Gas Separation Plant

A gas separation plant includes a de-ethanizer and a de-propanizer, which are distillation columns used to isolate ethane and propane, respectively, in natural gas liquids (NGL) and light ends fractionation in gas plants and refineries. The de-ethanizer removes ethane from a mixture of propane, butane and other heavier components. An output of the de-ethanizer is fed to a de-propanizer to separate propane from the mixture.

4. Amine Regeneration Plant

Hydrogen sulfide and carbon dioxide are the most common contaminants present in natural gas and are present in relatively larger quantities than other contaminants which can adversely impact the natural gas processing facility if not removed. Amine is used in an acid gas absorber and regenerator to sweeten sour gases in a chemical process in which a weak base (for example, the amine) reacts with weak acids such as hydrogen sulfide and carbon dioxide to form a weak salt.

5. Hydrocracking Plant

Hydrocracking is a two-stage process combining catalytic cracking and hydrogenation. In this process heavy feedstocks are cracked in the presence of hydrogen to produce more desirable products. The process employs high pressure, high temperature, a catalyst, and hydrogen. Hydrocracking is used for feedstocks that are difficult to process by either catalytic cracking or reforming, since these feedstocks are characterized usually by high polycyclic aromatics content or high concentrations of the two principal catalyst poisons, sulfur and nitrogen compounds (or combinations of them).

The hydrocracking process depends on the nature of the feedstock and the relative rates of the two competing reactions, hydrogenation and cracking. Heavy aromatics feedstock is converted into lighter products under a wide range of high pressures and high temperatures in the presence of hydrogen and special catalysts. When the feedstock has a high paraffinic content, hydrogen prevents the formation of polycyclic aromatics compounds. Hydrogen also reduces tar formation and prevents buildup of coke on the catalyst. Hydrogenation additionally converts sulfur and nitrogen compounds present in the feedstock to hydrogen sulfide and ammonia. Hydrocracking produces iso-butane for alkylation feedstock, and also performs isomerization for pour-point control and smoke-point control, both of which are important in high-quality jet fuel.

6. Diesel Hydrotreating Plant

Hydrotreating is a refinery process for reducing sulfur, nitrogen and aromatics while enhancing cetane number, density and smoke point. Hydrotreating assists the refining industry's efforts to meet the global trend for stringent clean fuels specifications, the growing demand for transportation fuels and the shift toward diesel. In this process, fresh feed is heated and mixed with hydrogen. Reactor effluent exchanges heat with the combined feed and heats recycle gas and stripper charge. Sulphide (for example, ammonium bisulphide and hydrogen sulphide) is then removed from the feed.

7. Sour Water Stripper Utility Plant (SWSUP)

The SWSUP receives sour water streams from acid gas removal, sulfur recovery, and flare units, and the sour gas stripped and released from the soot water flash vessel. The SWSUP strips the sour components, primarily carbon dioxide ($CO_2$), hydrogen sulfide ($H_2S$) and ammonia ($NH_3$), from the sour water stream.

8. Sulfur Recovery Plant

Sulfur recovery facilities in refineries operate to regulate the discharge of sulfur compounds to the atmosphere to meet environmental regulations. In a sulfur recovery plant, combustion products that include sulfur can be processed, for example, by heating, cooling with condensers, using sulfur conversion catalyst, and by other processing techniques. One technique is to use amines to extract the sulfur and other acid gas compounds.

9. Naphtha Hydrotreating Plant and Continuous Catalytic Reformer Plants

A Naphtha Hydrotreater (NHT) produces 101 Research Octane Number (RON) reformate, with a maximum 4.0 psi (pounds per square inch) Reid Vapor Pressure (RVP), as a blending stock in the gasoline pool. It usually has the flexibility to process blends of Naphtha from the Crude Unit, Gas Condensate Splitter, Hydrocracker, Light Straight-Run Naphtha (LSRN) and Visbreaker Plants. The NHT processes naphtha to produce desulfurized feed for the CCR platformer and gasoline blending.

Heat Exchangers

In the configurations described in this disclosure, heat exchangers are used to transfer heat from one medium (for example, a stream flowing through a plant in a crude oil refining facility, a buffer fluid or other medium) to another medium (for example, a buffer fluid or different stream flowing through a plant in the crude oil facility). Heat exchangers are devices which transfer (exchange) heat typically from a hotter fluid stream to a relatively less hotter fluid stream. Heat exchangers can be used in heating and cooling applications, for example, in refrigerators, air conditions or other cooling applications. Heat exchangers can be distinguished from one another based on the direction in which liquids flow. For example, heat exchangers can be parallel-flow, cross-flow or counter-current. In parallel-flow heat exchangers, both fluid involved move in the same direction, entering and exiting the heat exchanger side-by-side. In cross-flow heat exchangers, the fluid path runs perpendicular to one another. In counter-current heat exchangers, the fluid paths flow in opposite directions, with one fluid exiting whether the other fluid enters. Countercurrent heat exchangers are sometimes more effective than the other types of heat exchangers.

In addition to classifying heat exchangers based on fluid direction, heat exchangers can also be classified based on their construction. Some heat exchangers are constructed of multiple tubes. Some heat exchangers include plates with room for fluid to flow in between. Some heat exchangers enable heat exchange from liquid to liquid, while some heat exchangers enable heat exchange using other media.

Heat exchangers in crude oil refining and petrochemical facilities are often shell and tube type heat exchangers which include multiple tubes through which liquid flows. The tubes are divided into two sets—the first set contains the liquid to be heated or cooled; the second set contains the liquid responsible for triggering the heat exchange, that is, the fluid that either removes heat from the first set of tubes by absorbing and transmitting the heat away or warms the first set by transmitting its own heat to the liquid inside. When designing this type of exchanger, care must be taken in determining the correct tube wall thickness as well as tube diameter, to allow optimum heat exchange. In terms of flow, shell and tube heat exchangers can assume any of three flow path patterns.

Heat exchangers in crude oil refining and petrochemical facilities can also be plate and frame type heat exchangers. Plate heat exchangers include thin plates joined together with a small amount of space in between, often maintained by a rubber gasket. The surface area is large, and the corners of each rectangular plate feature an opening through which fluid can flow between plates, extracting heat from the plates as it flows. The fluid channels themselves alternate hot and cold liquids, meaning that the heat exchangers can effectively cool as well as heat fluid. Because plate heat exchangers have large surface area, they can sometimes be more effective than shell and tube heat exchangers.

Other types of heat exchangers can include regenerative heat exchangers and adiabatic wheel heat exchangers. In a regenerative heat exchanger, the same fluid is passed along both sides of the exchanger, which can be either a plate heat exchanger or a shell and tube heat exchanger. Because the fluid can get very hot, the exiting fluid is used to warm the incoming fluid, maintaining a near constant temperature. Energy is saved in a regenerative heat exchanger because the process is cyclical, with almost all relative heat being transferred from the exiting fluid to the incoming fluid. To maintain a constant temperature, a small quantity of extra energy is needed to raise and lower the overall fluid temperature. In the adiabatic wheel heat exchanger, an intermediate liquid is used to store heat, which is then transferred to the opposite side of the heat exchanger. An adiabatic wheel consists of a large wheel with threats that rotate through the liquids—both hot and cold—to extract or transfer heat. The heat exchangers described in this disclosure can include any one of the heat exchangers described earlier, other heat exchangers, or combinations of them.

Each heat exchanger in each configuration can be associated with a respective thermal duty (or heat duty). The thermal duty of a heat exchanger can be defined as an amount of heat that can be transferred by the heat exchanger from the hot stream to the cold stream. The amount of heat can be calculated from the conditions and thermal properties of both the hot and cold streams. From the hot stream point of view, the thermal duty of the heat exchanger is the product of the hot stream flow rate, the hot stream specific heat, and a difference in temperature between the hot stream inlet temperature to the heat exchanger and the hot stream outlet temperature from the heat exchanger. From the cold stream point of view, the thermal duty of the heat exchanger is the product of the cold stream flow rate, the cold stream specific heat and a difference in temperature between the cold stream outlet from the heat exchanger and the cold stream inlet temperature from the heat exchanger. In several applications, the two quantities can be considered equal assuming no heat loss to the environment for these units, particularly, where the units are well insulated. The thermal duty of a heat exchanger can be measured in watts (W), megawatts (MW), millions of British Thermal Units per hour (Btu/hr), or millions of kilocalories per hour (Kcal/h). In the configurations described here, the thermal duties of the heat exchangers are provided as being "about X MW," where "X" represents a numerical thermal duty value. The numerical thermal duty value is not absolute. That is, the actual thermal duty of a heat exchanger can be approximately equal to X, greater than X or less than X.

Configurations in which heat exchangers are described as being in series can have multiple implementations. In some implementations, the heat exchangers can be arranged in series in one order (for example, a first heat exchanger, a second heat exchanger and a third heat exchanger in that order) while in other implementations, the heat exchangers can be arranged in series in a different order (for example, a third heat exchanger, a first heat exchanger and a second heat exchanger in that order). In other words, a first heat exchanger described as being in series with and downstream of a second heat exchanger in one implementation can be in series with and upstream of the second heat exchanger in a second, different implementation.

Flow Control System

In each of the configurations described later, process streams (also called "streams") are flowed within each plant in a crude oil refining facility and between plants in the crude oil refining facility. The process streams can be flowed using one or more flow control systems implemented throughout the crude oil refining facility. A flow control system can include one or more flow pumps to pump the process streams, one or more flow pipes through which the process streams are flowed and one or more valves to regulate the flow of streams through the pipes.

In some implementations, a flow control system can be operated manually. For example, an operator can set a flow rate for each pump and set valve open or close positions to regulate the flow of the process streams through the pipes in the flow control system. Once the operator has set the flow rates and the valve open or close positions for all flow control systems distributed across the crude oil refining facility, the flow control system can flow the streams within a plant or between plants under constant flow conditions, for example, constant volumetric rate or other flow conditions. To change the flow conditions, the operator can manually operate the flow control system, for example, by changing the pump flow rate or the valve open or close position.

In some implementations, a flow control system can be operated automatically. For example, the flow control system can be connected to a computer system to operate the flow control system. The computer system can include a computer-readable medium storing instructions (such as flow control instructions and other instructions) executable by one or more processors to perform operations (such as flow control operations). An operator can set the flow rates and the valve open or close positions for all flow control systems distributed across the crude oil refining facility using the computer system. In such implementations, the operator can manually change the flow conditions by providing inputs through the computer system. Also, in such implementations, the computer system can automatically (that is, without manual intervention) control one or more of the flow control systems, for example, using feedback systems implemented in one or more plants and connected to the computer system. For example, a sensor (such as a pressure sensor, temperature sensor or other sensor) can be connected to a pipe through which a process stream flows. The sensor can monitor and provide a flow condition (such as a pressure, temperature, or other flow condition) of the process stream to the computer system. In response to the flow condition exceeding a threshold (such as a threshold pressure value, a threshold temperature value, or other threshold value), the computer system can automatically perform operations. For example, if the pressure or temperature in the pipe exceeds the threshold pressure value or the threshold temperature value, respectively, the computer system can provide a signal to the pump to decrease a flow rate, a signal to open a valve to relieve the pressure, a signal to shut down process stream flow, or other signals.

This disclosure describes advanced energy efficient configurations and the related processing schemes for medium grade semi-conversion grassroots and existing crude oil refining facilities.

A semi-conversion medium grade crude oil refining facility is one that does not include an aromatics complex. This disclosure describes a waste heat recovery and reuse network for such a refining facility. As described later, waste heat can be recovered from one or more of the units in the refining facility. Such a refinery typically consumes several hundred megawatts of energy (for example, about 400 MW) in heating utilities. Implementing the configurations described here can not only reduce energy consumption but also reduce energy-based greenhouse gas (GHG) emissions. In particular, this disclosure describes a method implemented in a crude oil refining facility to heat multiple streams in multiple plants of a crude oil refining facility using one or more of a hydrocracking plant stream in a hydrocracking plant, a hydro-treating plant stream in a hydro-treating plant and a hydrogen plant stream in a hydrogen plant of the crude oil refining facility. Several configurations of process schemes for doing so are described later with reference to the following figures.

Configuration 1

FIGS. 1A-1L illustrate configurations and related scheme details for indirect heating multiple first streams in a first plant in the crude oil refining facility such as those present in a naphtha hydro-treating plant, a sour water stripper plant, an amine regeneration plant, a sulfur recovery plant and gas separation plant in the crude oil refining facility using a buffer fluid, for example, oil, water or other buffer fluid. In some implementations, multiple first streams in multiple first plants can be heated indirectly using multiple second streams in multiple second plants. In some implementations, the first plants are the naphtha hydrotreating plant, the sour water stripper plant, the amine regeneration plant, the sulfur recovery plant and the gas separation plant; the first streams are naphtha splitter bottoms, a sour water stripper bottoms, an amine regenerator bottoms, an acid gas regenerator bottoms, a de-ethanizer bottoms and a C3/C4 splitter bottoms streams; the multiple second plants include the hydrocracking plant, the diesel hydrotreating plant and the natural gas steam reforming hydrogen plant; and the multiple second plant streams include the diesel product, a hydrocracking plant feed stream to a second reaction stage cold high pressure separator, a hydrocracking plant stream to a first reaction stage cold high pressure separator, product stripper overhead stream, a kerosene pumparound stream, a kerosene product stream, a diesel stripper overheads, a diesel stripper bottoms and a low temperature shift (LTS) converter product streams.

The configurations illustrated in FIGS. 1A-1L thermally integrate these plants indirectly using the multiple second streams in a second plant such as those present in a hydrocracking plant, a diesel hydro-treating plant and a natural gas steam reforming hydrogen plant in the crude oil refining facility to reduce the crude oil refining facility's energy consumption (for example, heating and cooling utilities). For example, a reduction in energy consumption by about 135 MW can translate to about 34% of the energy consumption in the crude oil refining facility. As described later, in certain schemes, heat exchange between process streams can be implemented using an intermediate buffer fluid, for example, water, oil, or other buffer fluid. In certain other configurations, a process stream (for example, a hydrocracking plant stream or other process streams) can be used to directly heat another process stream (for example, a naphtha hydro-treating plant stream or other process stream).

Indirectly heating the streams can include heating the streams through a buffer fluid, for example, oil, water, or other buffer fluid. A buffer fluid (for example, high pressure water or an oil or other hydrocarbon) from a buffer fluid tank (for example, a hot water or hot oil tank) is flowed to the hydrocracking plant 312, the diesel hydro-treating plant 300 and a natural gas steam reforming hydrogen plant 308 in the crude oil refining facility. The buffer fluid can be flowed into the plant as a single stream and split into multiple streams or it can be flowed into the plant as multiple streams.

Figure 1C:
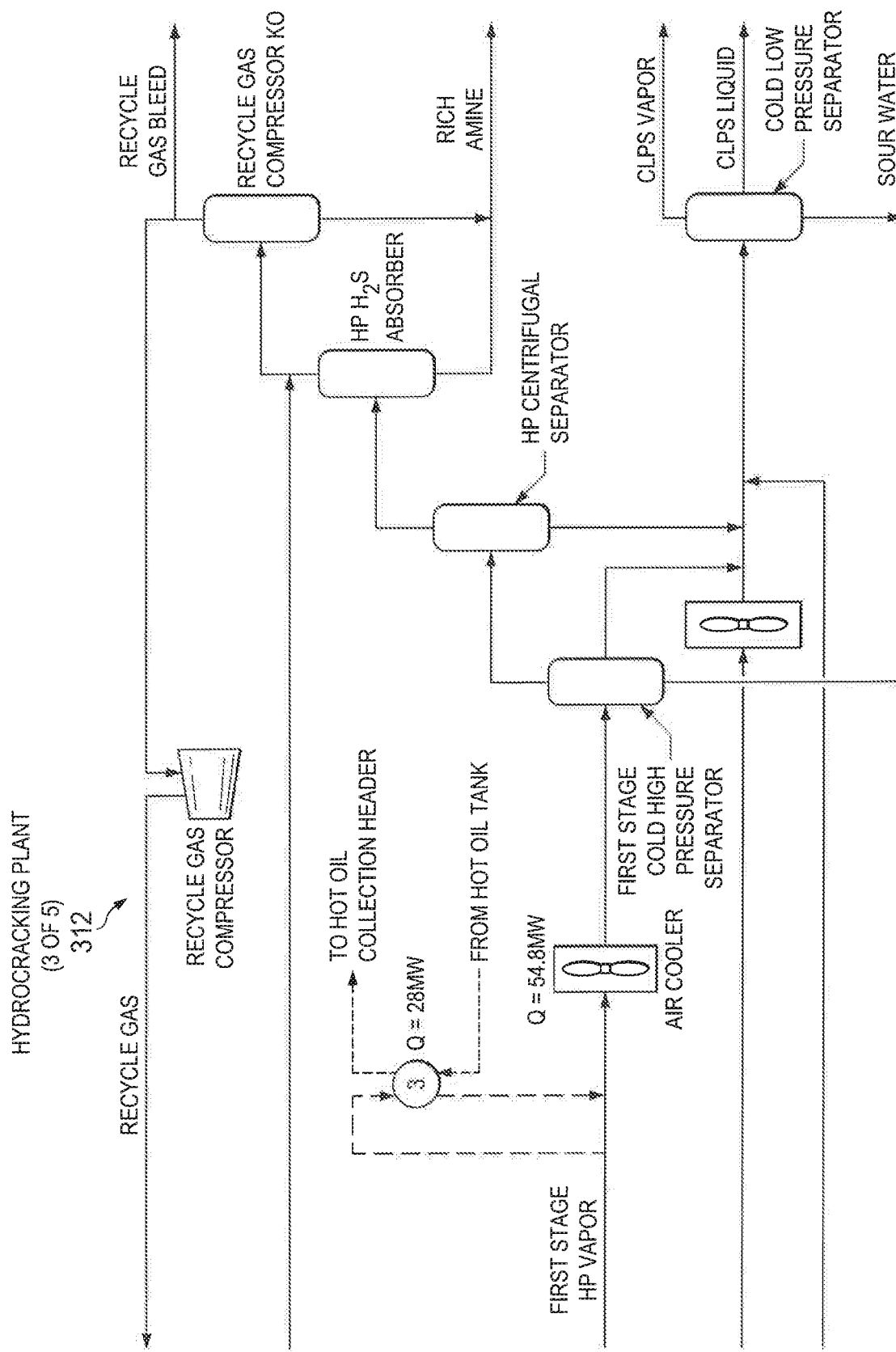
Figures 1, 1D:
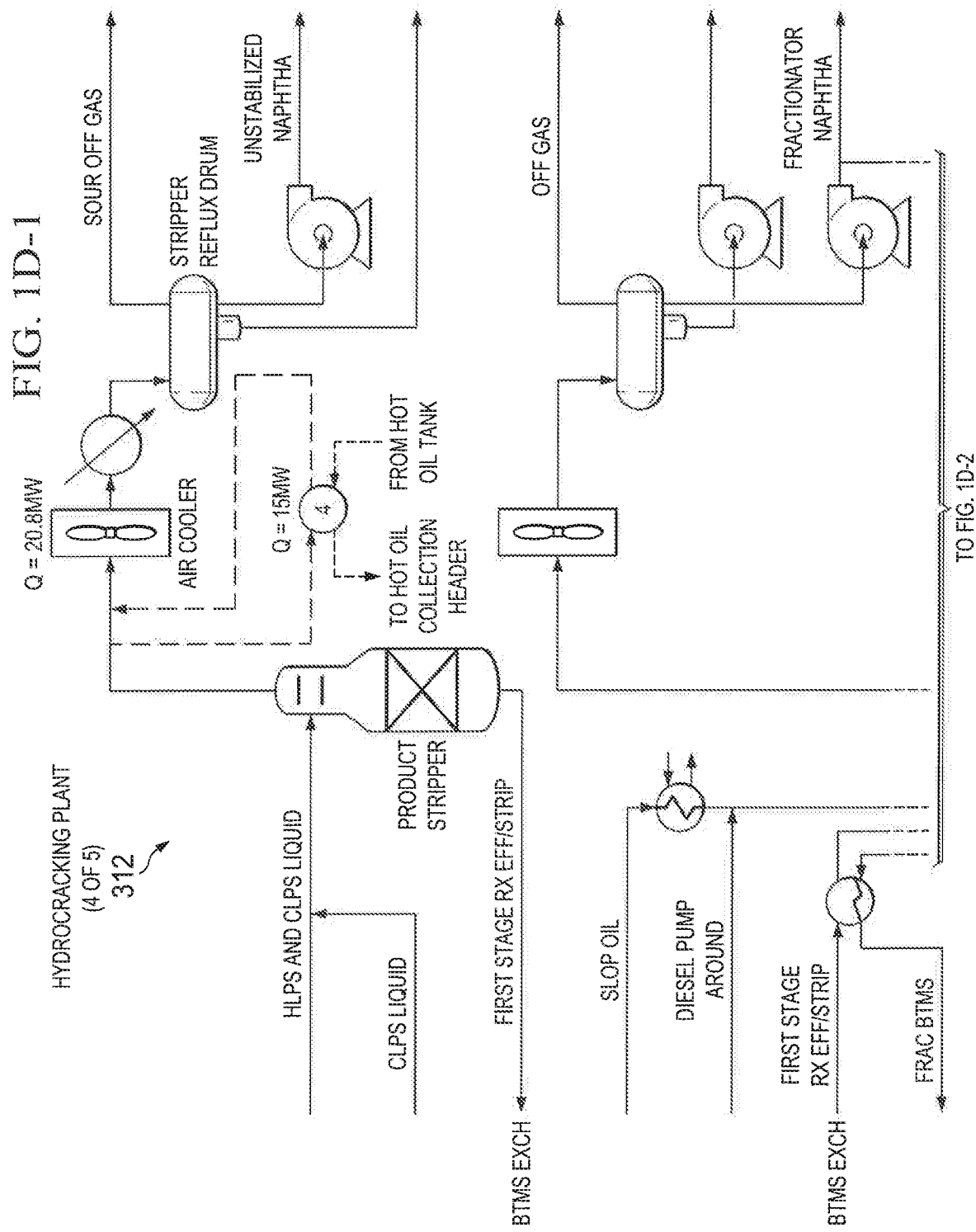
Figures 1, 1D, 2:
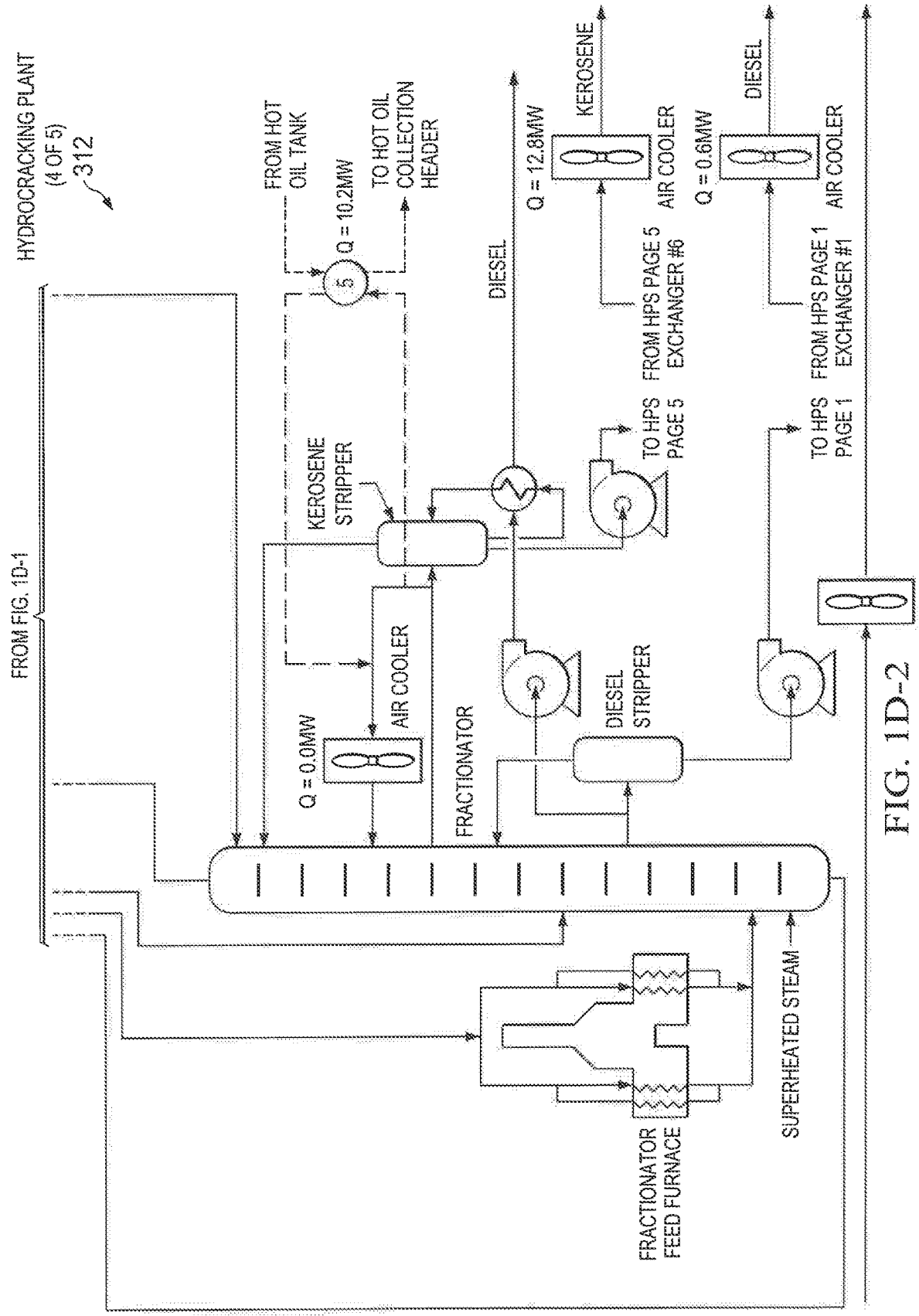
Figure 1E:
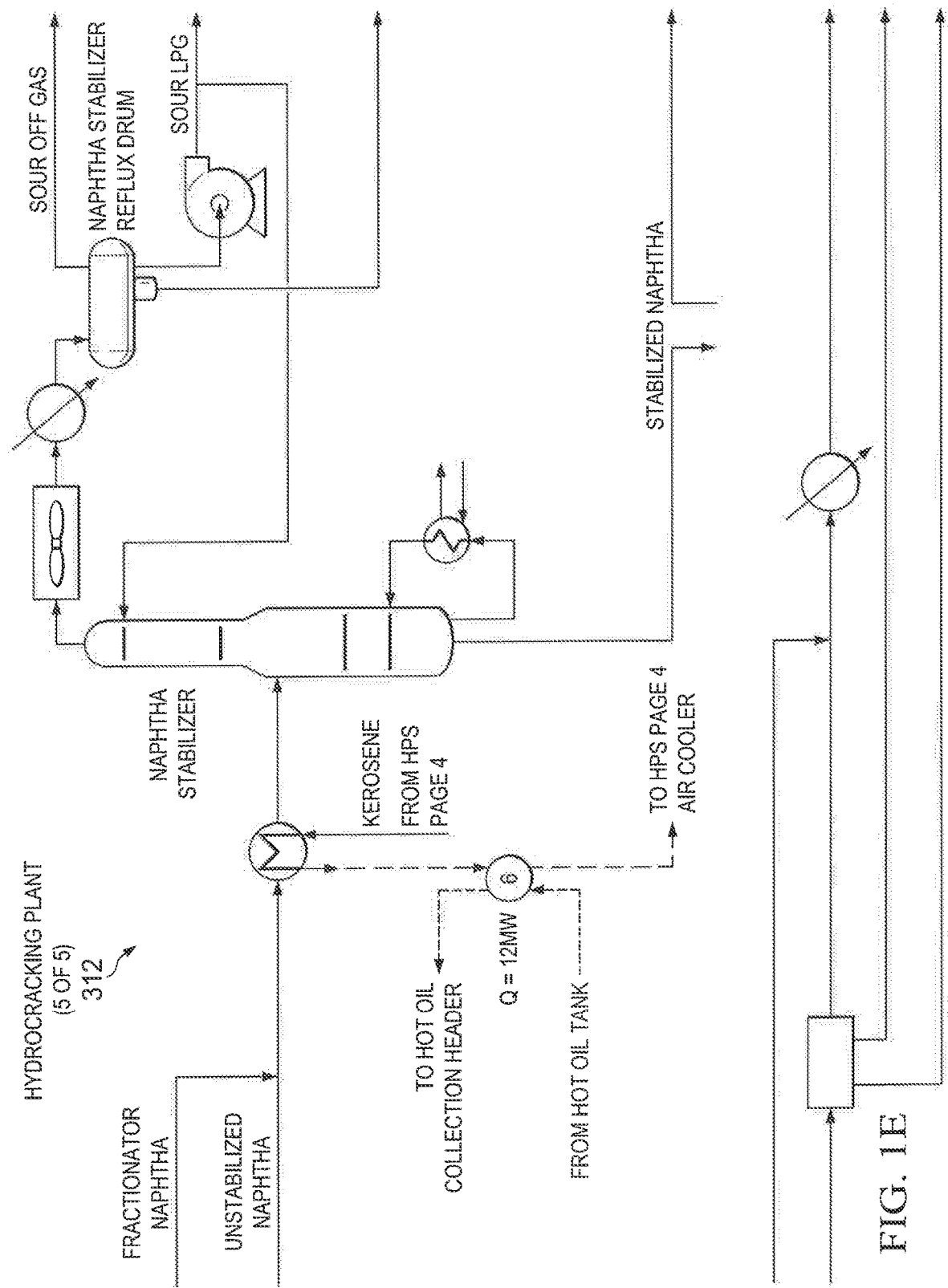

FIGS. 1A-1E show a hydrocracking plant 312 in a crude oil refinery facility. In some implementations, as shown in FIG. 1A, a diesel product stream heats a first buffer fluid stream in a first heat exchanger with a thermal load that can range between about 5 MW and 15 MW (for example, 11.6 MW). As shown in FIG. 1B, a hydrocracking plant feed stream to a second reaction stage cold high pressure separator heats a second buffer fluid stream in a second heat exchanger with a thermal duty that can range between about 5 MW and 15 MW (for example, 8.7 MW). As shown in FIG. 1C, a hydrocracking plant stream to a first reaction stage cold high pressure separator heats a third buffer fluid stream in a third heat exchanger with a thermal duty that can range between about 25 MW and 35 MW (for example, 28 MW). As shown in FIG. 1D-1, a product stripper overhead stream heats a fourth buffer fluid stream in a fourth heat exchanger with a thermal duty that can range between about 10 MW and 20 MW (for example, 15 MW). Also, as shown in FIG. 1D-2, a kerosene pumparound stream heats a fifth buffer fluid stream in a fifth heat exchanger with a thermal duty that can range between about 5 MW and 15 MW (for example, 10.2 MW). In this configuration the cooling requirement of the kerosene pumparound stream can be 0 MW because the alternative flow path disclosed in this configuration may satisfy the entire cooling requirement for the kerosene pumparound stream for the operation of the fractionator column. As shown in FIG. 1E, a kerosene product stream heats a sixth buffer fluid stream in a sixth heat exchanger with a thermal duty that can range between about 5 MW and 15 MW (for example, 12 MW). The diesel product stream, the hydrocracking plant feed stream to a second reaction stage cold high pressure separator, the hydrocracking plant stream to a first reaction stage cold high pressure separator, the product stripper overhead stream, the kerosene pumparound stream and the kerosene product stream are each returned to the hydrocracking plant 312 for further processing.

Figure 1F:
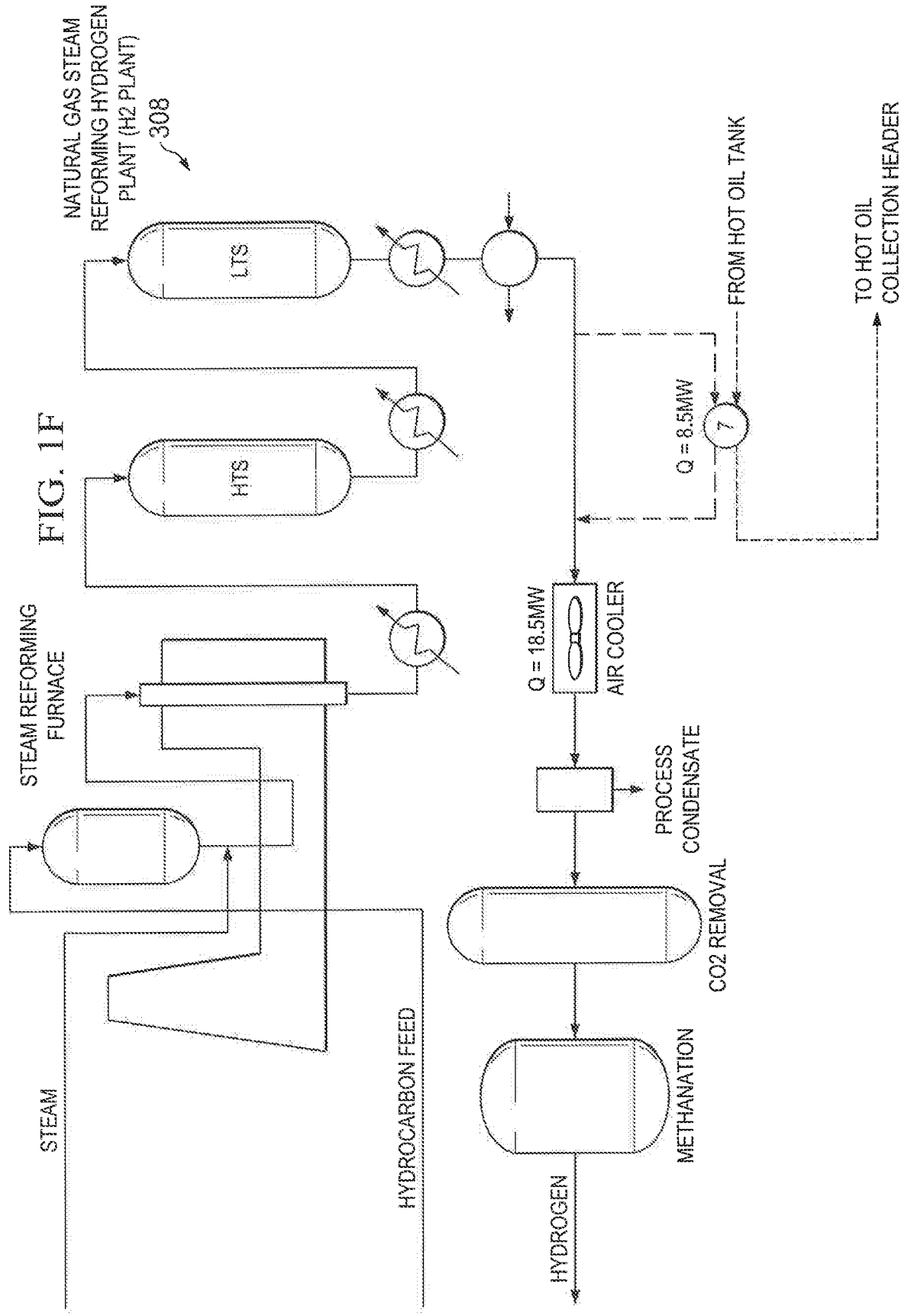
Figure 1G:
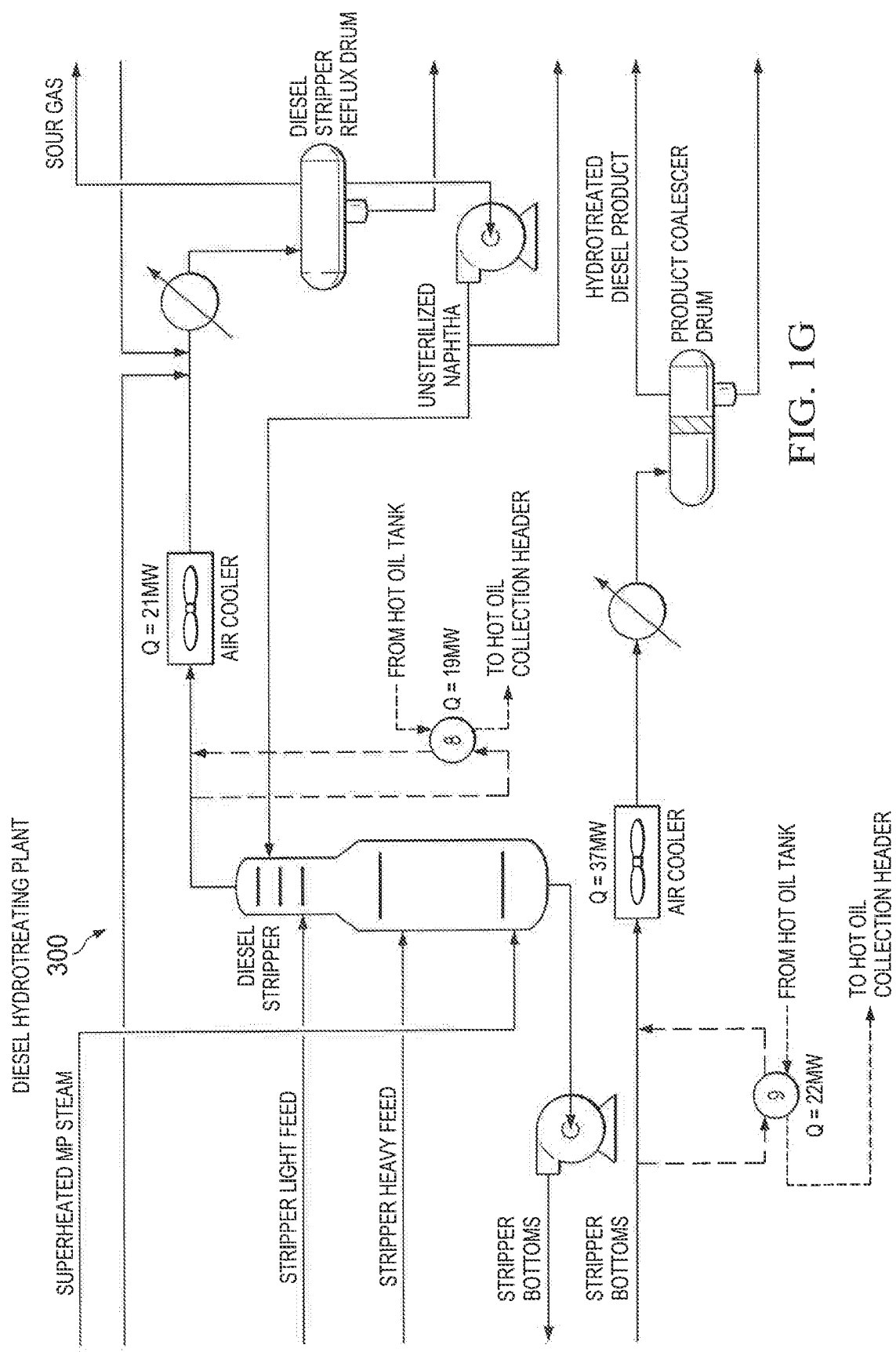

FIG. 1F shows a natural gas steam reforming hydrogen plant 308 in a crude oil refinery facility. The low temperature shift (LTS) converter product stream heats a seventh buffer fluid stream in a seventh heat exchanger with a thermal duty that can range between about 5 MW and 15 MW (for example, 8.5 MW). The LTS converter product stream is returned to the natural gas steam reforming hydrogen plant 308 for further processing FIG. 1G shows a diesel hydro-treating plant 300 in a crude oil refinery facility. The diesel stripper overhead stream heats an eighth buffer fluid stream in an eighth heat exchanger with a thermal duty that can range between about 15 MW and 25 MW (for example, 19 MW). Also, a diesel stripper bottoms stream heats a ninth buffer fluid stream in a ninth heat exchanger with a thermal duty that can range between about 15 MW and 25 MW (for example, 22 MW). The diesel stripper overhead stream and diesel stripper bottoms stream are each returned to the diesel hydro-treating plant 300 for further processing.

The first, second, third, fourth, fifth, sixth, seventh, eighth and ninth heat exchangers are coupled in parallel to each other relative to the flow of the buffer fluid stream. The transfer of heat from each process stream into each buffer fluid stream captures heat that would have otherwise been discharged to the environment.

The first, second, third, fourth, fifth, sixth, seventh, eighth and ninth heated buffer fluid streams are combined into a combined heated buffer fluid in a collection header. The combined heated buffer fluid from the collection header (or in some embodiments, a heated or insulated buffer fluid tank or storage unit that can hold heated collected buffer fluid for a period before use) can be flowed to the naphtha hydrotreating plant 314, the sour water stripper plant 310, the sulfur recovery plant 302, the amine regeneration plant 306 and the gas separation plant 304.

Figure 1H:
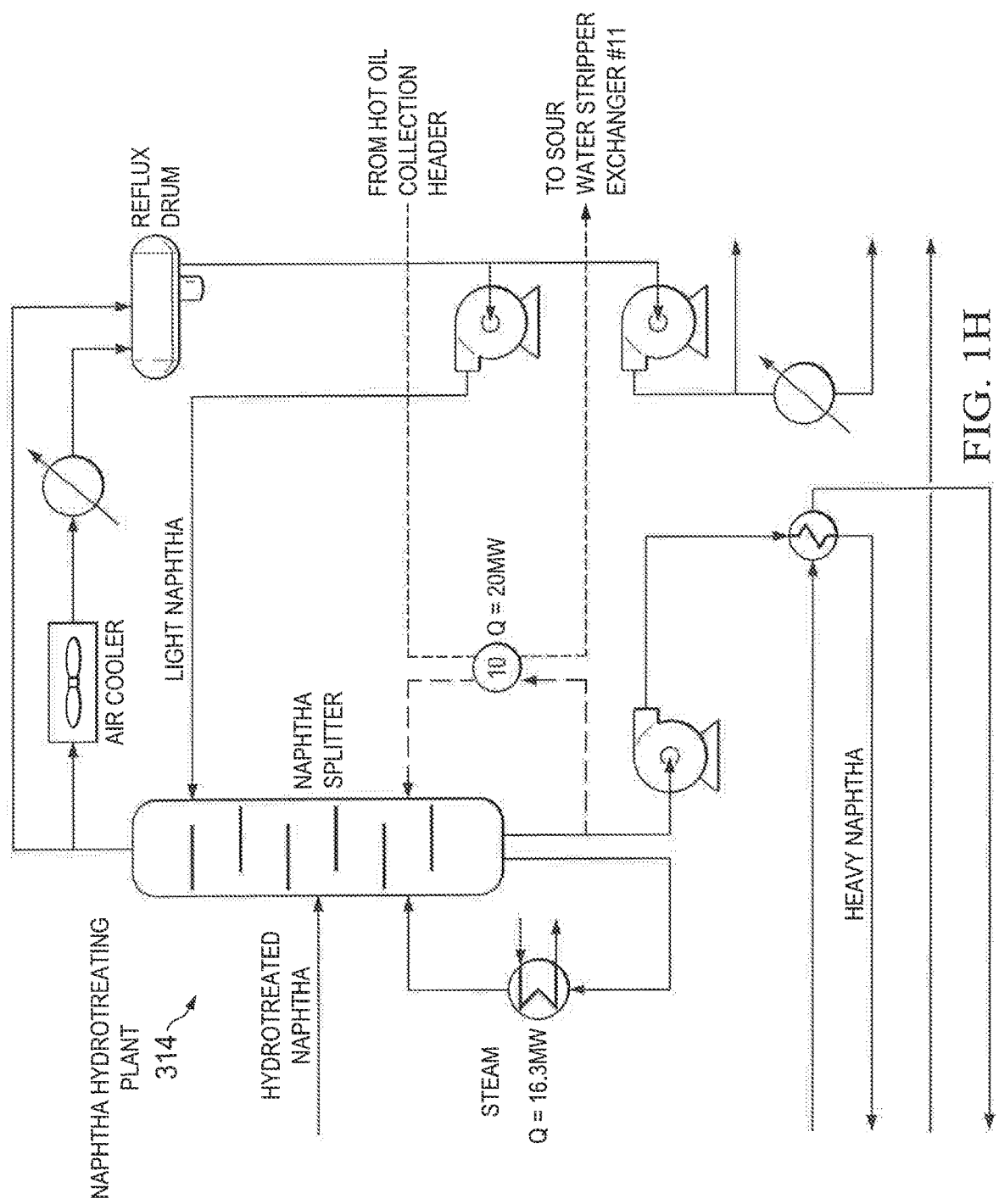
Figure 11:
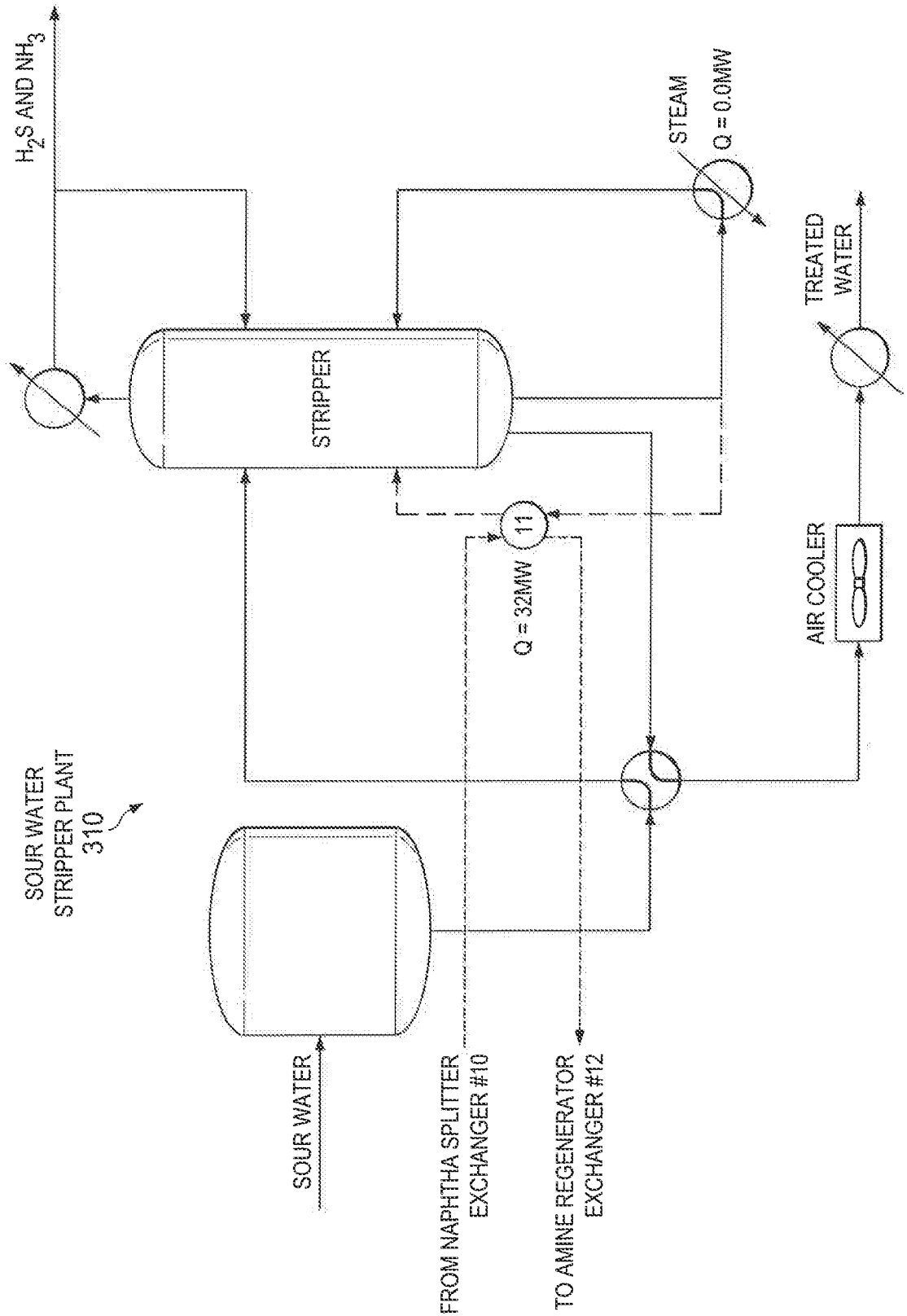

In an embodiment, the heated buffer fluid is flowed to the naphtha hydrotreating plant 314. FIG. 1H shows a naphtha hydro-treating plant 314 in a crude oil refinery facility. The naphtha splitter bottom stream is heated using the combined heated buffer fluid in a tenth heat exchanger with a thermal duty that can range between about 15 MW and 25 MW (for example, 20 MW). The tenth heat exchanger is coupled in series with and is downstream of the set of first, second, third, fourth, fifth, sixth, seventh, eighth and ninth heat exchangers relative to the flow of the combined heated buffer fluid. As shown in FIG. 1H, the steam heat input for the naphtha splitter column can be reduced because the alternative flow paths disclosed in this configuration may partially satisfy the heat load for the operation of the column. In an alternative embodiment, the steam heat input for the naphtha splitter column can be 0 MW because the alternative flow paths disclosed in this configuration may satisfy the entire heat load for the operation of the column.

FIG. 1I shows a sour water stripper plant 310 in a crude oil refinery facility. The combined heated buffer fluid exiting the tenth heat exchanger is flowed to the sour water stripper plant 310. The sour water stripper bottom stream is heated using the combined buffer fluid in an eleventh heat exchanger with a thermal duty that can range between about 25 MW and 35 MW (for example, 32 MW). The eleventh heat exchanger is coupled in series with and is downstream of the set of first, second, third, fourth, fifth, sixth, seventh, eighth and ninth heat exchangers relative to the flow of the combined heated buffer fluid. As shown in FIG. 1I, the steam heat input for the sour water stripper can be 0 MW because the alternative flow path disclosed in this configuration may satisfy the entire heat load for the operation of the column. In an alternative embodiment, the steam heat input for the sour water stripper can be reduced because the alternative flow path disclosed in this configuration may partially satisfy the heat load for the operation of the column.

Figure 1J:
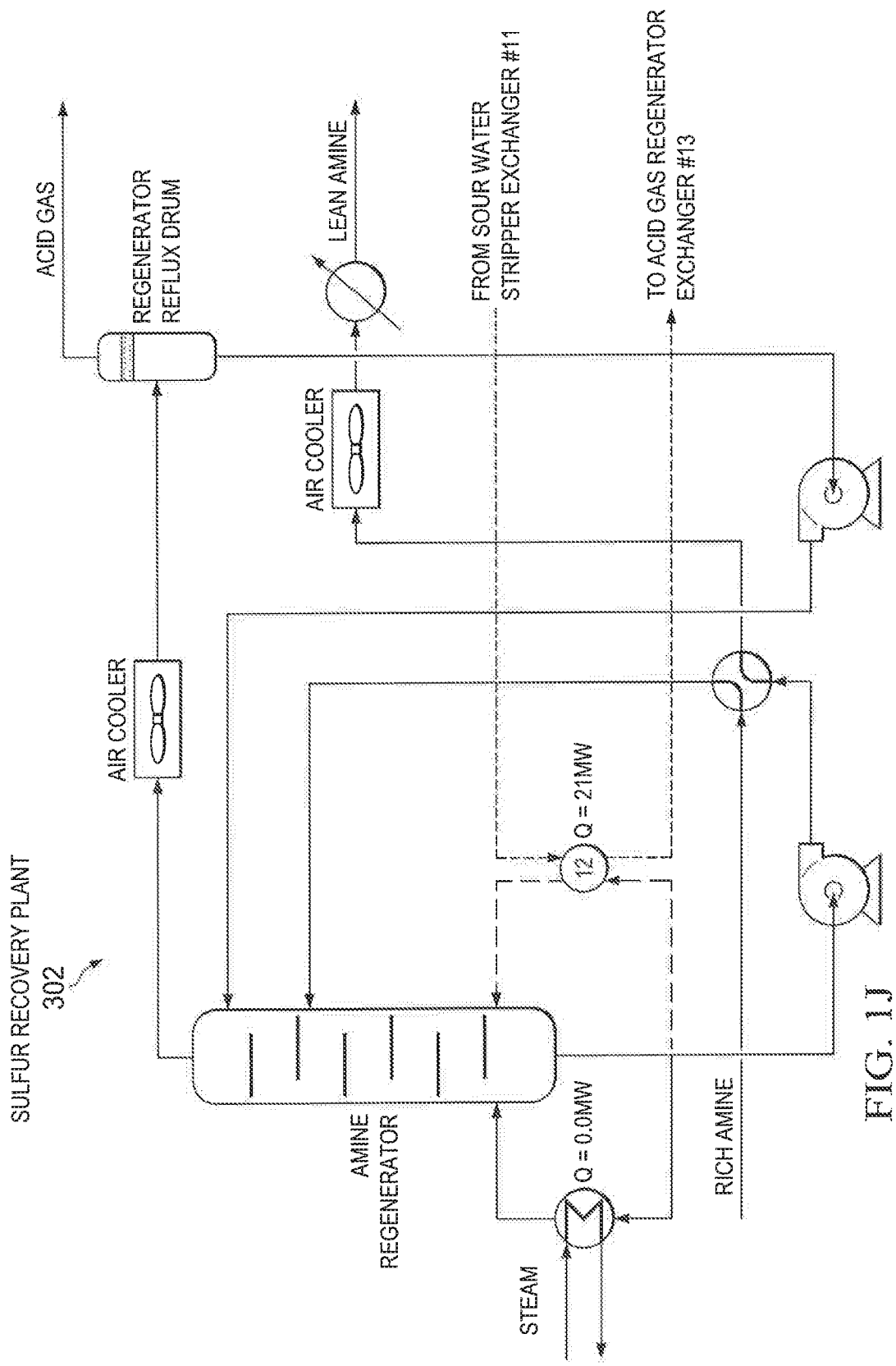

FIG. 1J shows a sulfur recovery plant 302 in a crude oil refinery facility. The combined heated buffer fluid exiting the eleventh heat exchanger is flowed to the sulfur recovery plant 302. The amine regenerator bottom stream is heated using the combined heated buffer fluid in a twelfth heat exchanger with a thermal duty that can range between about 15 MW and 25 MW (for example, 21 MW). The twelfth heat exchanger is coupled in series with and is downstream of the set of first, second, third, fourth, fifth, sixth, seventh, eighth and ninth heat exchangers relative to the flow of the combined heated buffer fluid. As shown in FIG. 1J, the steam heat input for the amine regenerator can be 0 MW because the alternative flow path disclosed in this configuration may satisfy the entire heat load for the operation of the column. In an alternative embodiment, the steam heat input for the amine regenerator can be reduced because the alternative flow path disclosed in this configuration may partially satisfy the heat load for the operation of the column.

Figure 1K:
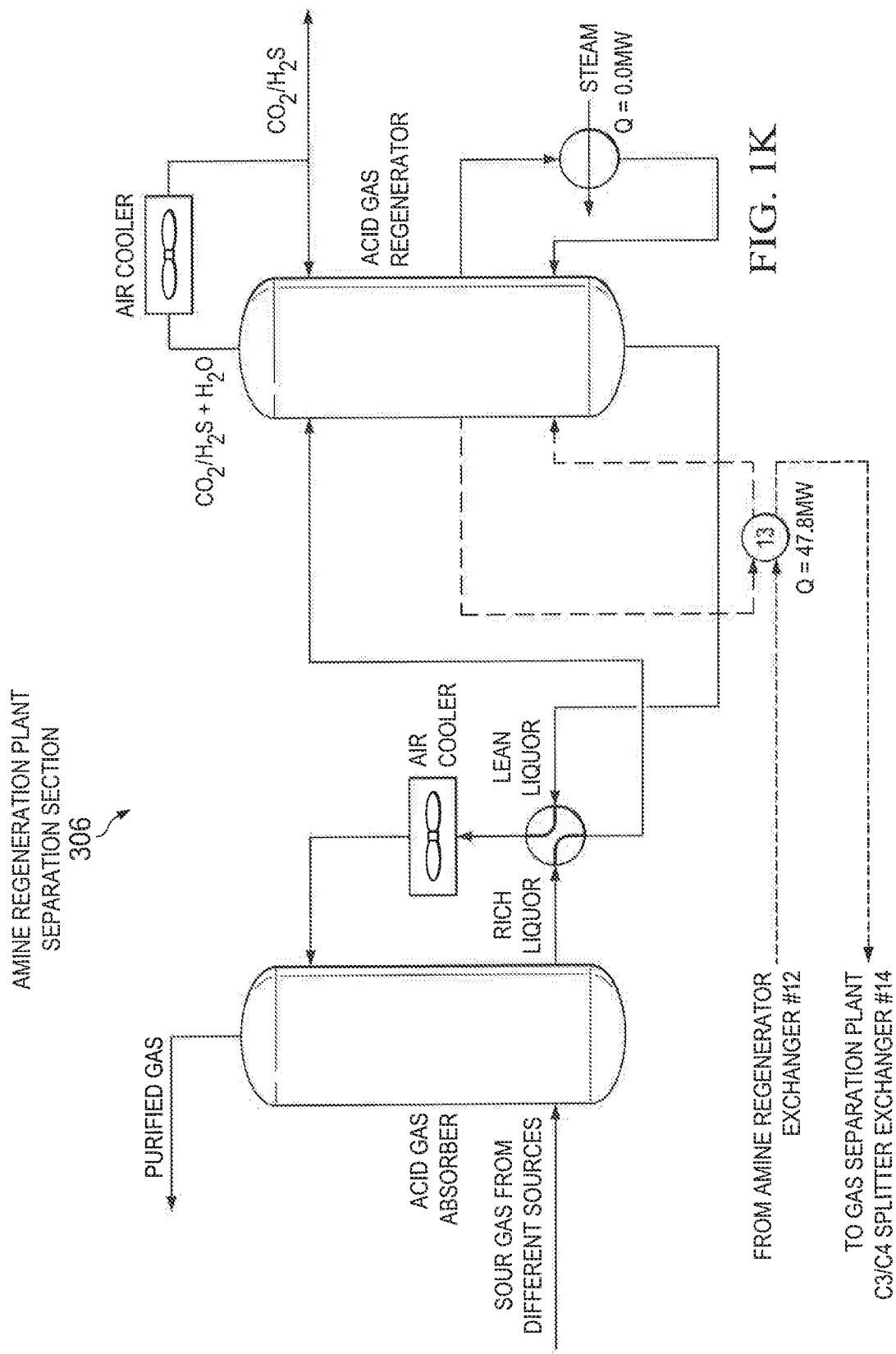

FIG. 1K shows an amine regeneration plant 306 in a crude oil refinery facility. The combined heated buffer fluid exiting the twelfth heat exchanger is flowed to the amine regeneration plant 306. The acid gas regenerator bottoms stream is heated using the combined heated buffer fluid in a thirteenth heat exchanger with a thermal duty that can range between about 45 MW and 55 MW (for example, 47.8 MW). The thirteenth heat exchanger is coupled in series with and is downstream of the set of first, second, third, fourth, fifth, sixth, seventh, eighth and ninth heat exchangers relative to the flow of the combined heated buffer fluid. As shown in FIG. 1K, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

Figure 1L:
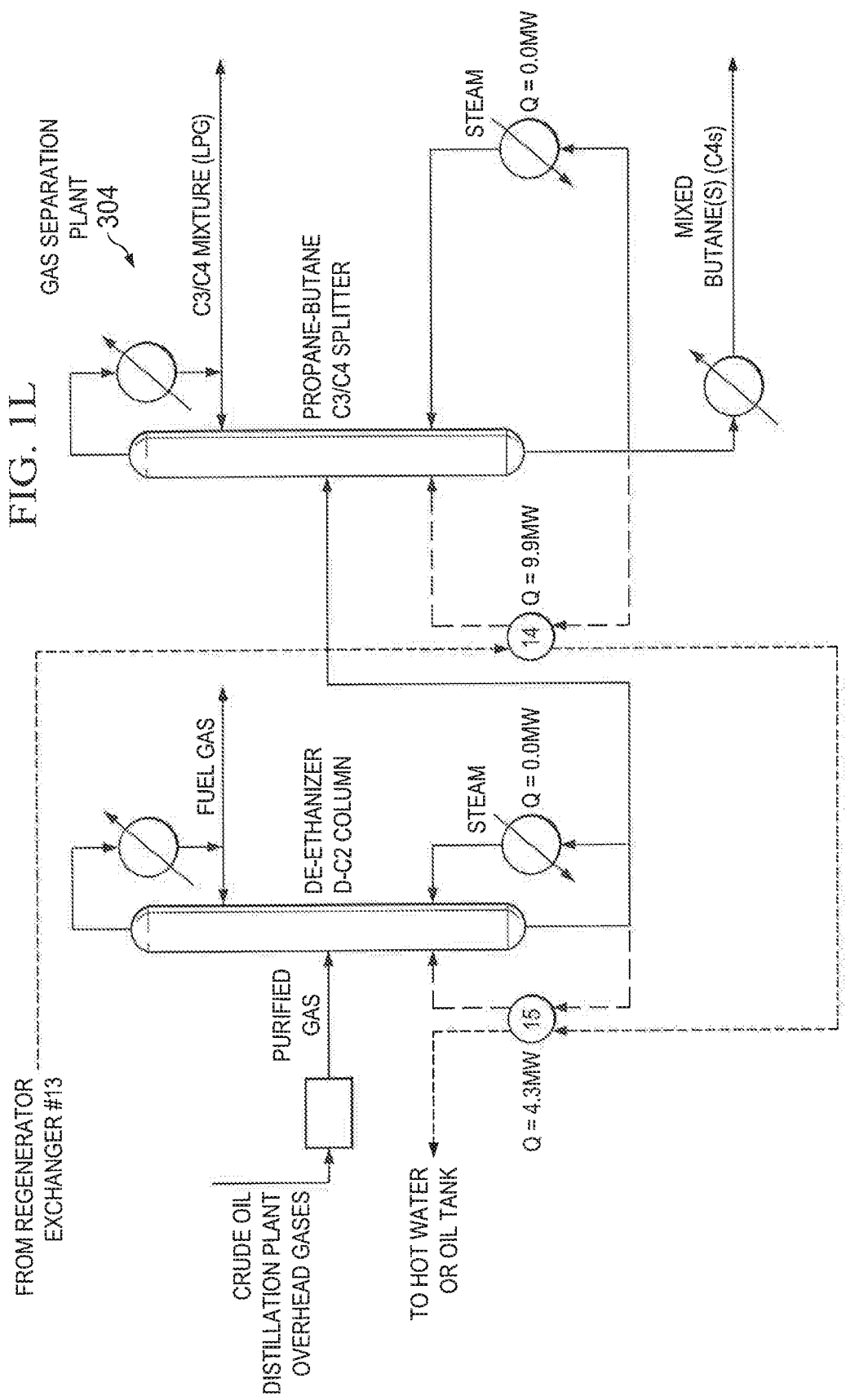

FIG. 1L shows a gas separation plant 304 in a crude oil refinery facility. The combined heated buffer fluid exiting the thirteenth heat exchanger is flowed to the gas separation plant 304. The C3/C4 splitter bottoms stream in the gas separation plant 304 is heated using the combined heated buffer fluid in a fourteenth heat exchanger with a thermal duty that can range between about 5 MW and 15 MW (for example, 9.9 MW). The fourteenth heat exchanger is coupled in series with and is downstream of the set of first, second, third, fourth, fifth, sixth, seventh, eighth and ninth heat exchangers relative to the flow of the combined heated buffer fluid. As shown in FIG. 1L, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

The combined heated buffer fluid exiting the fourteenth heat exchanger is flowed to the de-ethanizer column. The de-ethanizer bottoms stream in the gas separation plant 304 is heated using the combined heated buffer fluid in a fifteenth heat exchanger with a thermal duty that can range between about 1 MW and 10 MW (for example, 4.3 MW). The fifteenth heat exchanger is coupled in series with and is downstream of the set of first, second, third, fourth, fifth, sixth, seventh, eighth and ninth heat exchangers relative to the flow of the combined heated buffer fluid. As shown in FIG. 1L, the steam heat input for the de-ethanizer can be 0 MW because the alternative flow path disclosed in this configuration may satisfy the entire heat load for the operation of the column. In an alternative embodiment, the steam heat input for the de-ethanizer can be reduced because the alternative flow path disclosed in this configuration may partially satisfy the heat load for the operation of the column.

The heated buffer fluid exiting the fifteenth heat exchanger is flowed to the collection header or the buffer fluid tank. In this manner, the tenth heat exchanger, the eleventh heat exchanger, the twelfth heat exchanger, the thirteenth heat exchanger, the fourteenth heat exchanger and the fifteenth heat exchanger are fluidically coupled to each other in series.

In some implementations, the combined heated buffer fluid can be flowed in series through the different plants. For example, the combined heated buffer fluid is flowed first to the naphtha hydro-treating plant, then to the sour water stripper plant, then to the sulfur recovery plant, then to the amine regeneration plant separation section and then to the gas separation plant. The heated buffer fluid exiting the final heat exchanger(s) in this series can then be flowed to the buffer fluid tank. The buffer fluid from the buffer fluid tank can then be flowed to the different plants to restart the waste heat recovery and reuse cycle.

FIGS. 1A-1L show that such recovery and reuse of waste heat indirectly from the hydrocracking plant, the diesel hydro-treating plant and the natural gas steam reforming hydrogen plant can result in decreasing or eliminating the heat energy to heat the streams in the naphtha hydro-treating plant, the sour water stripper plant, the amine regeneration plant, the sulfur recovery plant and the gas separation plant or combinations of them such as by about 135 MW.

Configuration 2

In some implementations described with reference to FIGS. 1M-1Y, heat can be recovered from the hydrocracking plant and the diesel hydrotreating plant using both direct and indirect techniques. Heat can also be recovered directly from the natural gas steam reforming hydrogen plant. In some implementations, a first stream in a first plant can be directly heated using multiple second streams from two of multiple second plants, multiple third streams in multiple third plants can be indirectly heated using multiple second streams from all of the multiple second plants, and multiple fourth streams in a fourth plant can be directly heated using multiple second streams from all of the multiple second plants. In some implementations, the first stream is the naphtha splitter bottoms stream; the first plant is the naphtha hydrotreating plant; the multiple second plants are the hydrocracking plant, the diesel hydrotreating plant and the natural gas steam reforming hydrogen plant; the multiple second plant streams are the product stripper overheads stream, diesel product stream, kerosene product stream, kerosene pumparound stream, a feed stream to a second reaction stage cold high pressure separator, a feed stream to a first reaction stage cold high pressure separator, diesel stripper overhead stream, diesel stripper bottoms stream and low temperature shift (LTS) converter product stream; the multiple third plants include the sour water stripper plant, the sulfur recovery plant and the amine regeneration plant; the multiple third streams include the sour waters stripper bottoms, the amine regenerator bottoms, and the acid gas regenerator bottoms streams; the fourth plant is the gas separation plant; and the fourth plant streams include the C3/C4 splitter bottoms and the de-ethanizer bottoms streams.

The configurations illustrated in FIGS. 1M-1Y thermally integrate different plants in the crude oil refining facility to reduce the crude oil refining facility's energy consumption (for example, heating and cooling utilities). For example, a reduction in energy consumption by about 140 MW can translate to about 35% of the energy consumption in the crude oil refining facility. In certain configurations, a process stream (for example, a hydrocracking plant stream or other process streams) can be used to directly heat another process stream (for example, a naphtha hydro-treating plant stream or other process stream). In certain configurations, heat exchange between process streams can be implemented using an intermediate buffer fluid, for example, water, oil, or other buffer fluid. As described later, the configuration describes a hybrid scheme in which some waste energy is recovered indirectly (that is, using a buffer fluid) and some waste energy is recovered directly (that is, from a process stream).

In some implementations, a naphtha hydrotreating plant can be heated directly by both the hydrocracking plant and the diesel hydrotreating plant. FIGS. 1T and 1U show a naphtha hydrotreating plant 814 in a crude oil refining facility. FIG. 1S shows a diesel hydrotreating plant 300 in a crude oil refining facility. The naphtha stripper bottoms stream can be flowed into the plant as a single stream and split into multiple streams or it can be flowed into the plant as multiple streams. The naphtha stripper bottoms stream is split into a first, a second, a third, a fourth, a fifth, and a sixth stream. A first naphtha splitter bottom stream can be directly heated using a diesel stripper overhead stream in heat exchanger A with a thermal duty that can range between about 5 MW and 15 MW (for example, 7.46 MW). Also, as shown in FIG. 1S, a second naphtha splitter bottoms stream can be directly heated using diesel stripper bottoms stream in heat exchanger B with a thermal duty that can range between about 1 MW and 10 MW (for example, 1.8 MW). The transfer of heat directly to another process stream captures heat that would have otherwise been discharged to the environment.

Figure 1N:
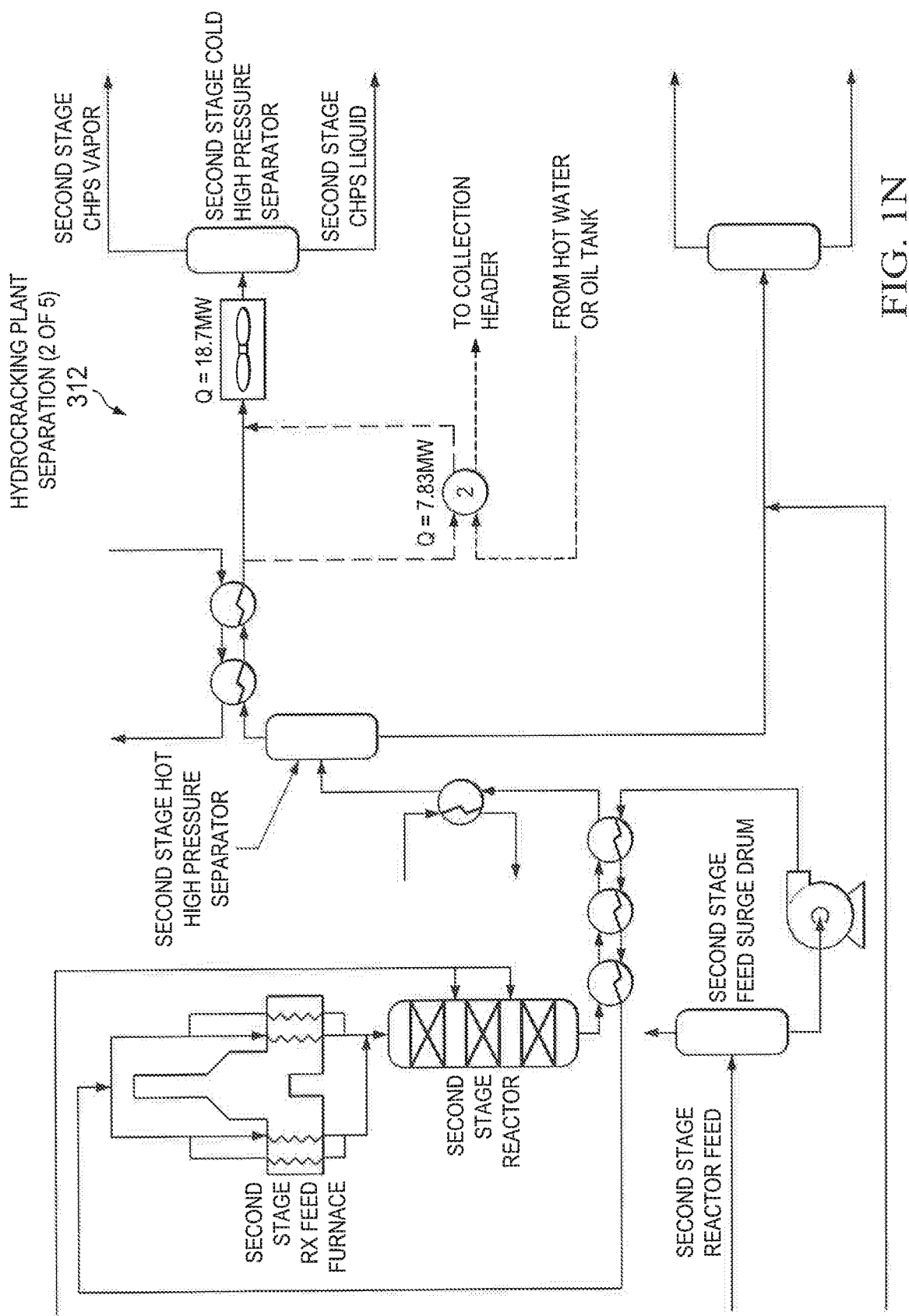
Figure 10:
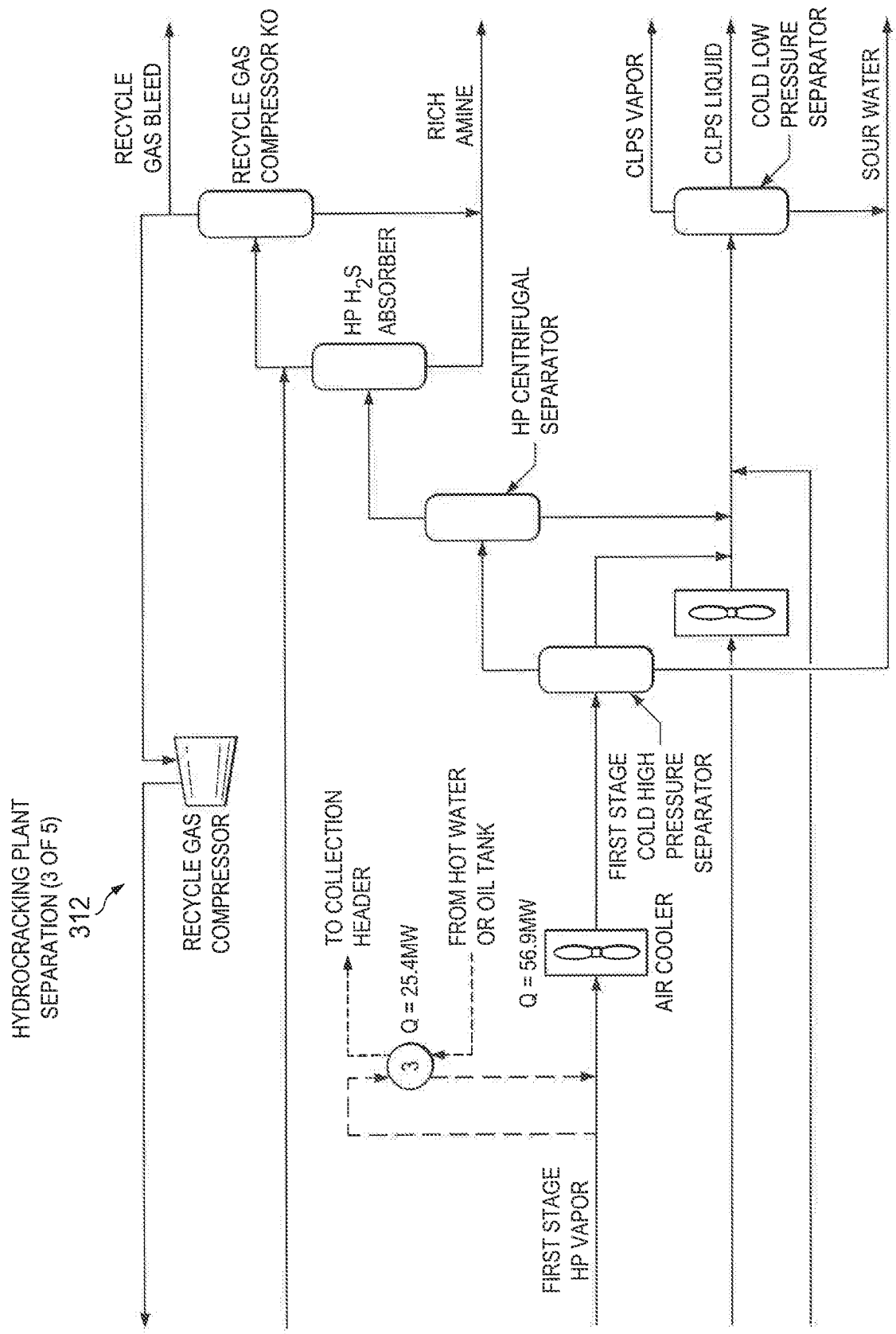
Figures 1, 1P:
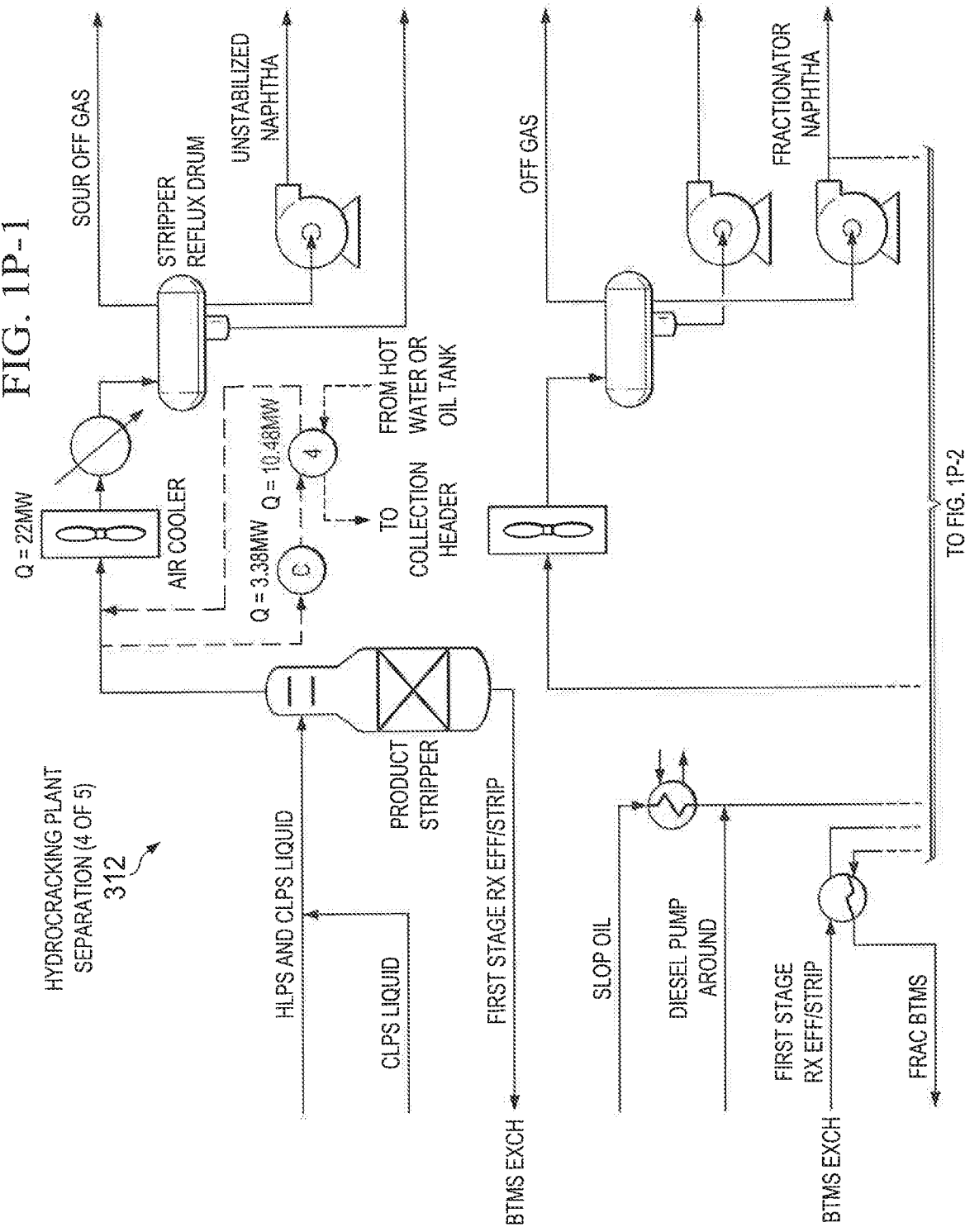
Figures 1, 1P, 2:
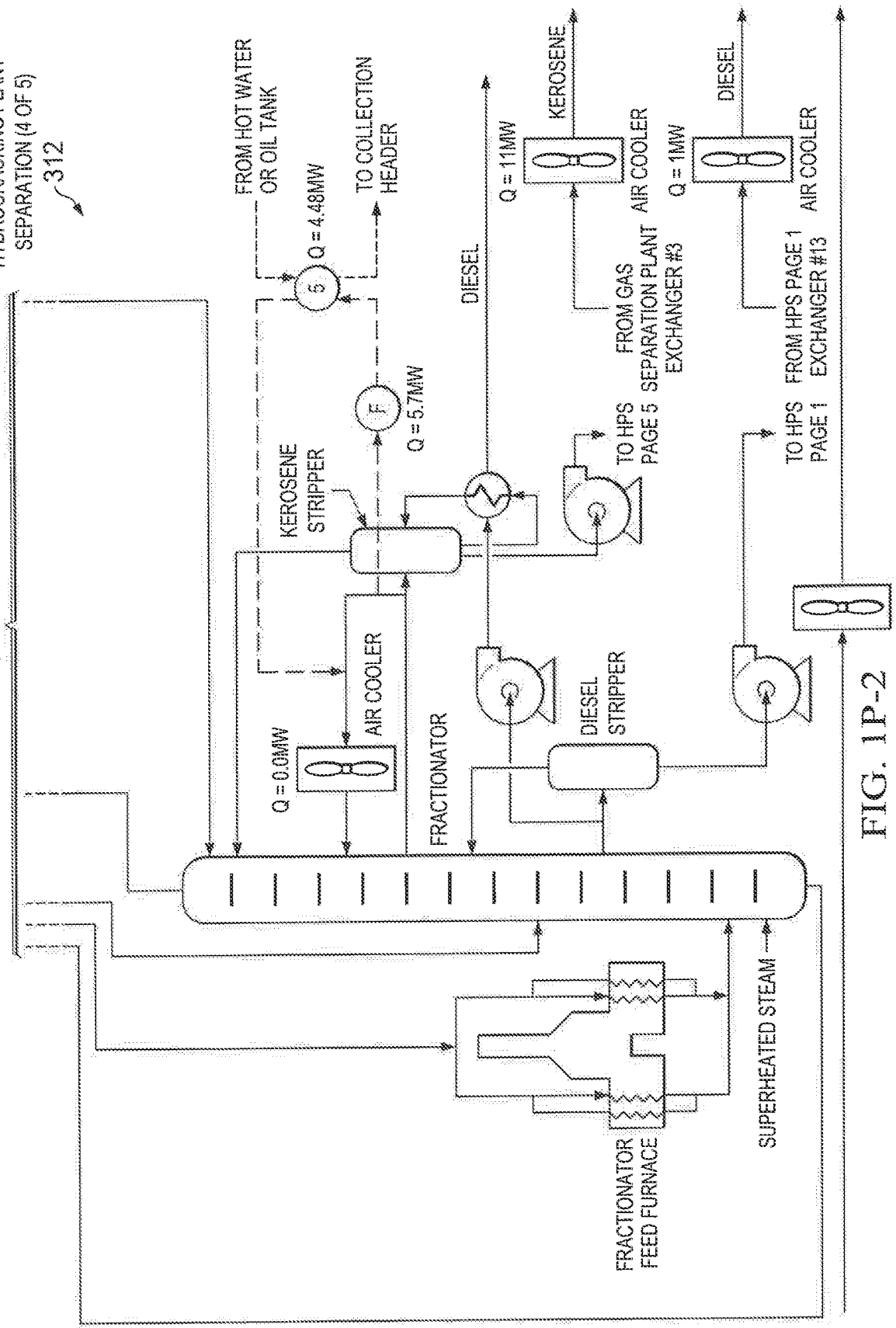
Figure 1Q:
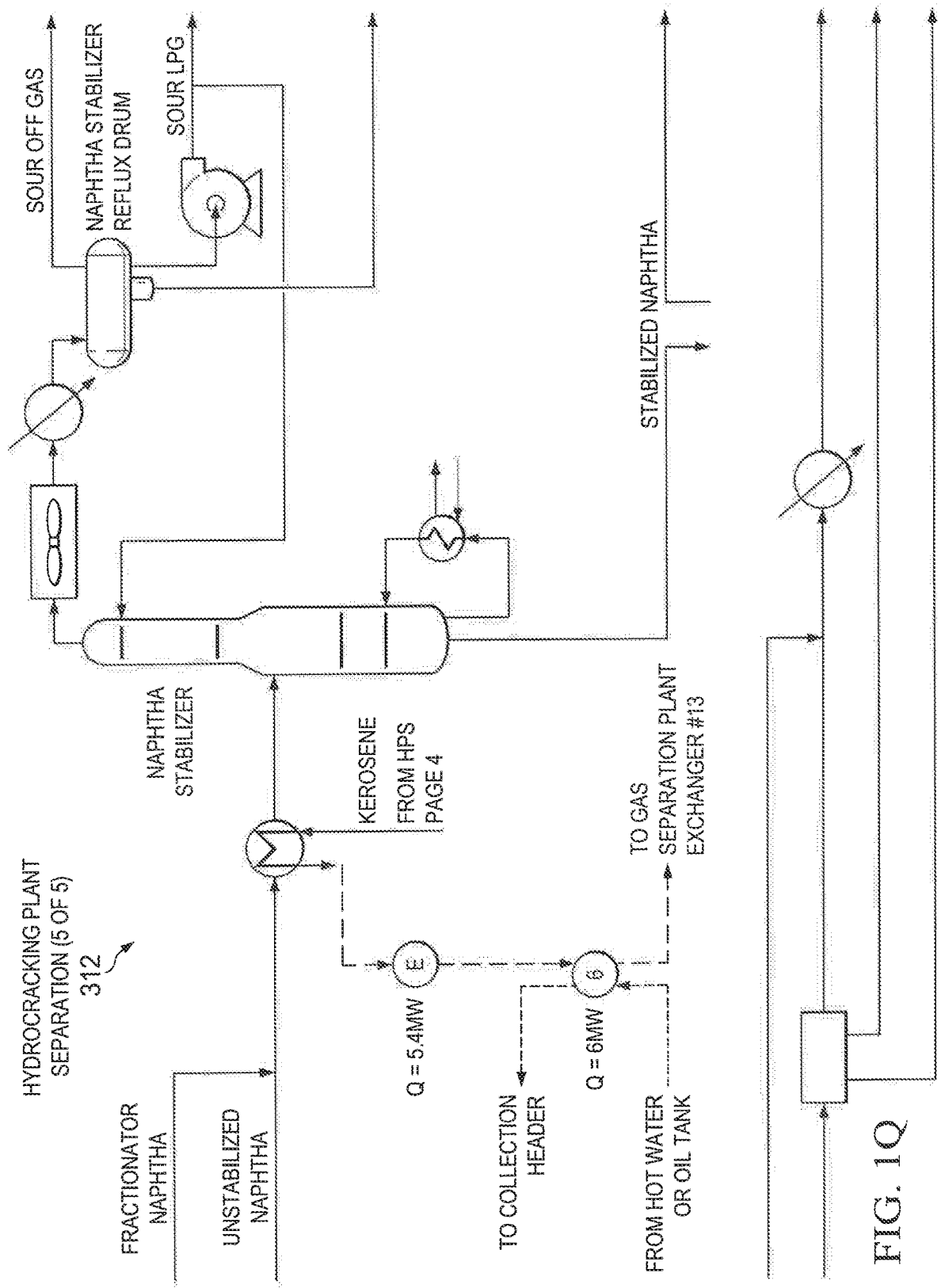

FIGS. 1M-1Q show a hydrocracking plant 312 in a crude oil refining facility. As shown in FIG. 1P-1, a third naphtha splitter bottoms stream can be directly heated using product stripper overheads stream in heat exchanger C with a thermal duty that can range between about 1 MW and 10 MW (for example, 3.38 MW). As shown in FIG. 1M, a fourth naphtha splitter bottoms stream can be directly heated using the diesel product stream in heat exchanger D with a thermal duty that can range between about 1 MW and 10 MW (for example, 6.6 MW). As shown in FIG. 1Q, a fifth naphtha splitter bottoms stream can be directly heated using kerosene product stream in heat exchanger E with a thermal duty that can range between about 1 MW and 10 MW (for example, 5.4 MW). As shown in FIG. 1P-2, a sixth naphtha splitter bottoms stream can be heated using the kerosene pumparound stream in heat exchanger F with a thermal duty that can range between about 1 MW and 10 MW (for example, 5.7 MW). The transfer of heat directly to another process stream captures heat that would have otherwise been discharged to the environment.

The A, B, C, D, E and F heat exchangers are coupled in parallel to each other relative to the flow of the naphtha splitter bottoms stream. The heated first, the heated second, the heated third, the heated fourth, the heated fifth and the heated sixth streams are combined resulting in a combined heated naphtha splitter bottom stream.

FIGS. 1T and 1U show the naphtha hydrotreating plant 314 in a crude oil refining facility. The combined heated naphtha splitter bottom stream is then flowed to the naphtha hydro-treating plant 314. As shown in FIGS. 1T and 1U, the steam heat input for the naphtha splitter column can be reduced because the alternative flow paths disclosed in this configuration may partially satisfy the heat load for the operation of the column. In an alternative embodiment, the steam heat input for the naphtha splitter column can be 0 MW because the alternative flow paths disclosed in this configuration may satisfy the entire heat load for the operation of the column.

In some implementations, a sour water stripper plant, a sulfur recovery plant and an amine regeneration plant can be indirectly heated using the hydrocracking plant, the diesel hydrotreating plant, and the natural gas steam reforming hydrogen plant. Indirectly heating the streams can include heating the streams through a buffer fluid, for example, oil, water, or other buffer fluid. A buffer fluid (for example, high pressure water or an oil or other hydrocarbon) from a buffer fluid tank (for example, a hot water or hot oil tank) is flowed to the hydrocracking plant 312, the diesel hydro-treating plant 300 and a natural gas steam reforming hydrogen plant 308 in the crude oil refining facility. The buffer fluid can be flowed into the plant as a single stream and split into multiple streams or it can be flowed into the plant as multiple streams.

Buffer fluid is flowed to the hydrocracking plant 312. As shown in FIG. 1M, a first buffer fluid stream is heated using a diesel product stream in a first heat exchanger with a thermal duty that can range between about 1 MW and 10 MW (for example, 4.56 MW). The first heat exchanger is coupled in series with and is downstream of the D heat exchanger relative to the flow of the diesel product stream. As shown in FIG. 1N, a second buffer fluid stream is heated using a feed stream to a second reaction stage cold high pressure separator in a second heat exchanger with a thermal duty that can range between about 5 MW and 15 MW (for example, 7.83 MW). As shown in FIG. 1O, a third buffer fluid stream is heated using a feed stream to a first reaction stage cold high pressure separator in a third heat exchanger with a thermal duty that can range between about 20 MW and 30 MW (for example, 25.4 MW). As shown in FIG. 1P-1, a fourth buffer fluid stream is heated using a product stripper overhead stream in a fourth heat exchanger with a thermal duty that can range between about 5 MW and 15 MW (for example, 10.48 MW). The fourth heat exchanger is coupled in series with and is downstream of the C heat exchanger relative to the flow of the product stripper overheads stream. Also, as shown in FIG. 1P-2, a fifth buffer fluid stream is heated using a kerosene pumparound stream in a fifth heat exchanger with a thermal duty that can range between about 1 MW and 10 MW (for example, 4.48 MW). The fifth heat exchanger is coupled in series with and is downstream of the F heat exchanger relative to the flow of the product stripper overhead stream. As shown in FIG. 1P-2, in this configuration the cooling requirement of the kerosene pumparound stream can be 0 MW because the alternative flow path disclosed in this configuration may satisfy the entire cooling requirement for the kerosene pumparound stream for the operation of the fractionator column. As shown in FIG. 1Q, a sixth buffer fluid stream is heated using a kerosene product stream in a sixth heat exchanger with a thermal duty that can range between about 1 MW and 10 MW (for example, 6 MW). The sixth heat exchanger is coupled in series with and is downstream of the E heat exchanger relative to the flow of the kerosene product stream. The transfer of heat from these process streams into the buffer fluid captures heat that would have otherwise been discharged to the environment. Each of the diesel product stream, the feed stream to a second reaction stage cold high pressure separator, the feed stream to a first reaction stage cold high pressure separator, the product stripper overhead stream and the kerosene pumparound stream are returned to the hydrocracking plant 312 for further processing.

In some implementations, the diesel products stream can be flowed in series through the different plants in a different order. For example, the diesel products stream can be flowed first to the first heat exchanger to heat the buffer fluid and then to heat exchanger D to heat one of the naphtha hydrotreating plant 314 naphtha splitter bottoms streams. As well, the product stripper overheads stream can be flowed in series through the different plants in a different order. For example, the diesel products stream can be flowed first to the fourth heat exchanger to heat the buffer fluid and then to heat exchanger C to heat one of the naphtha hydrotreating plant 314 naphtha splitter bottoms streams. In addition, the kerosene pumparound stream can be flowed in series through the different plants in a different order. For example, the kerosene pumparound stream can be flowed first to the fifth heat exchanger to heat the buffer fluid and then to heat exchanger F to heat one of the naphtha hydrotreating plant 314 naphtha splitter bottoms streams.

Figure 1R:
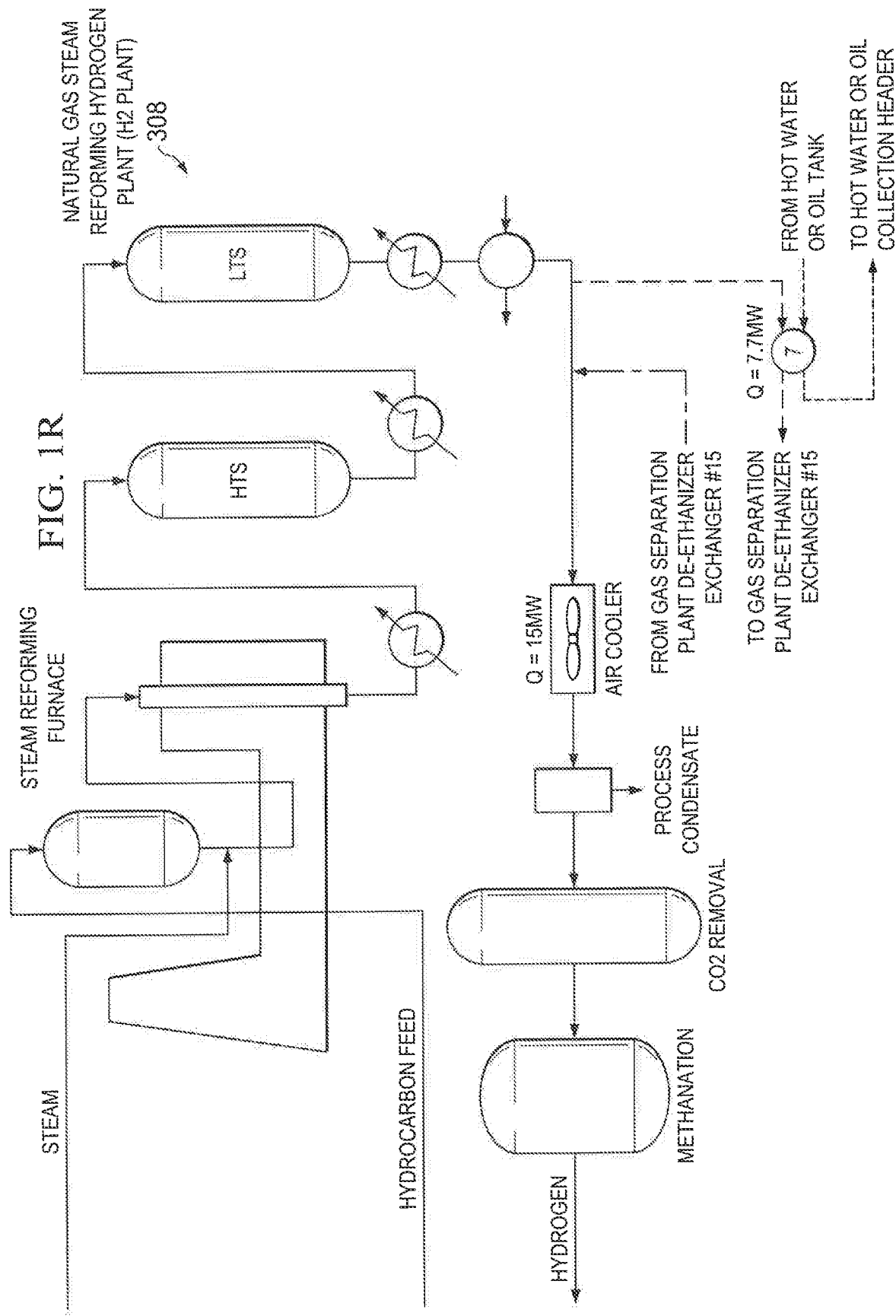
Figure 1S:
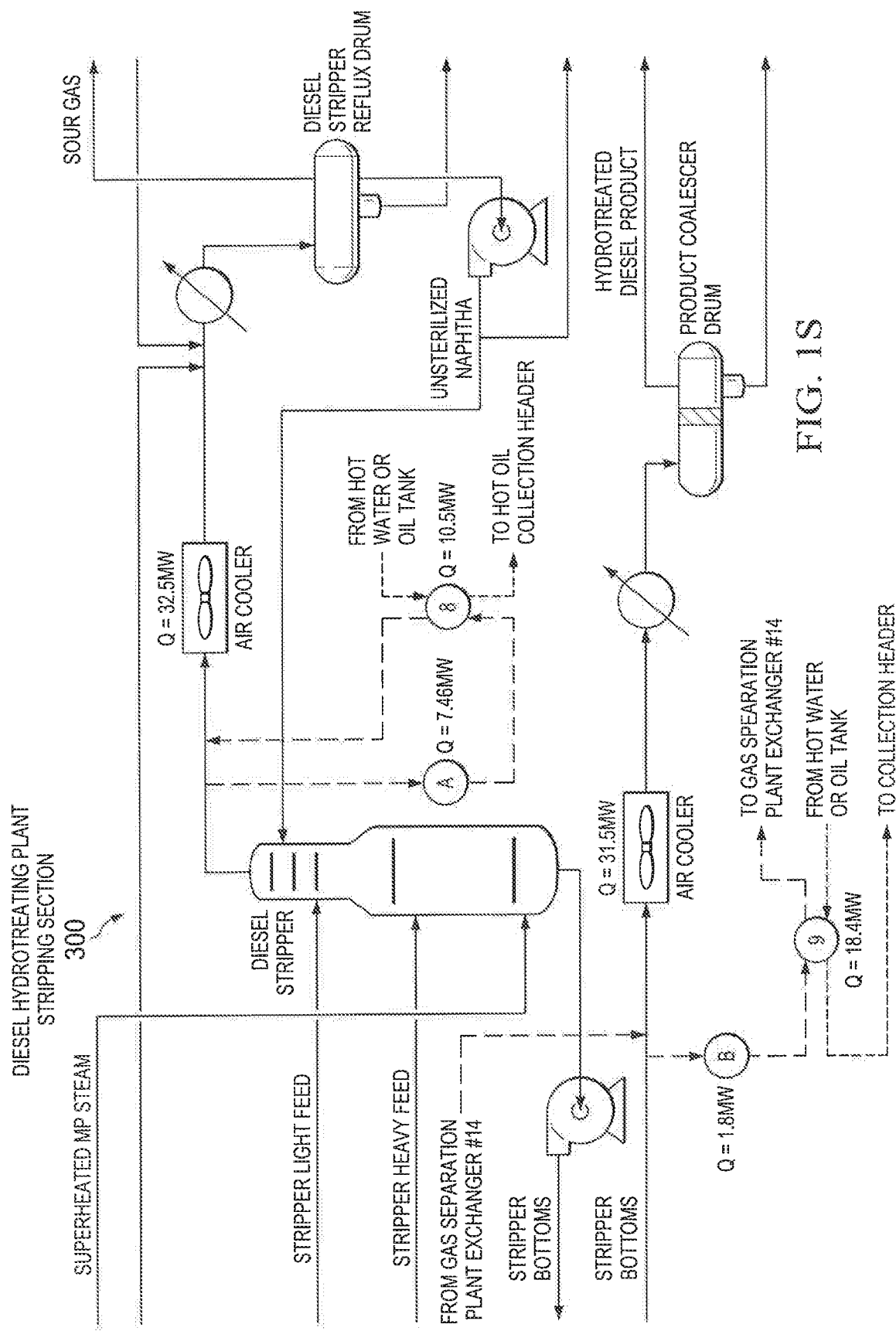
Figure 1T:
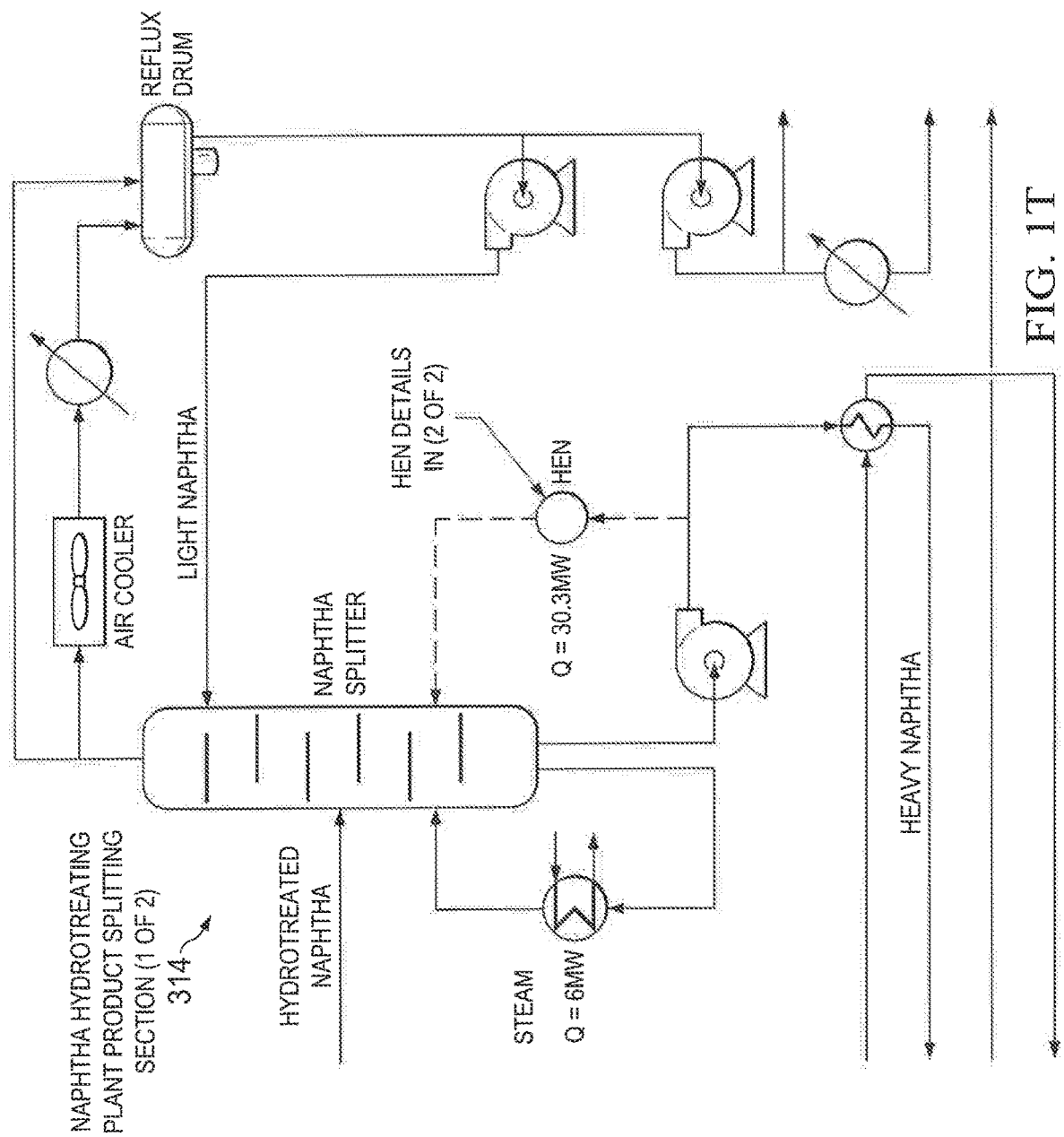
Figure 1U:
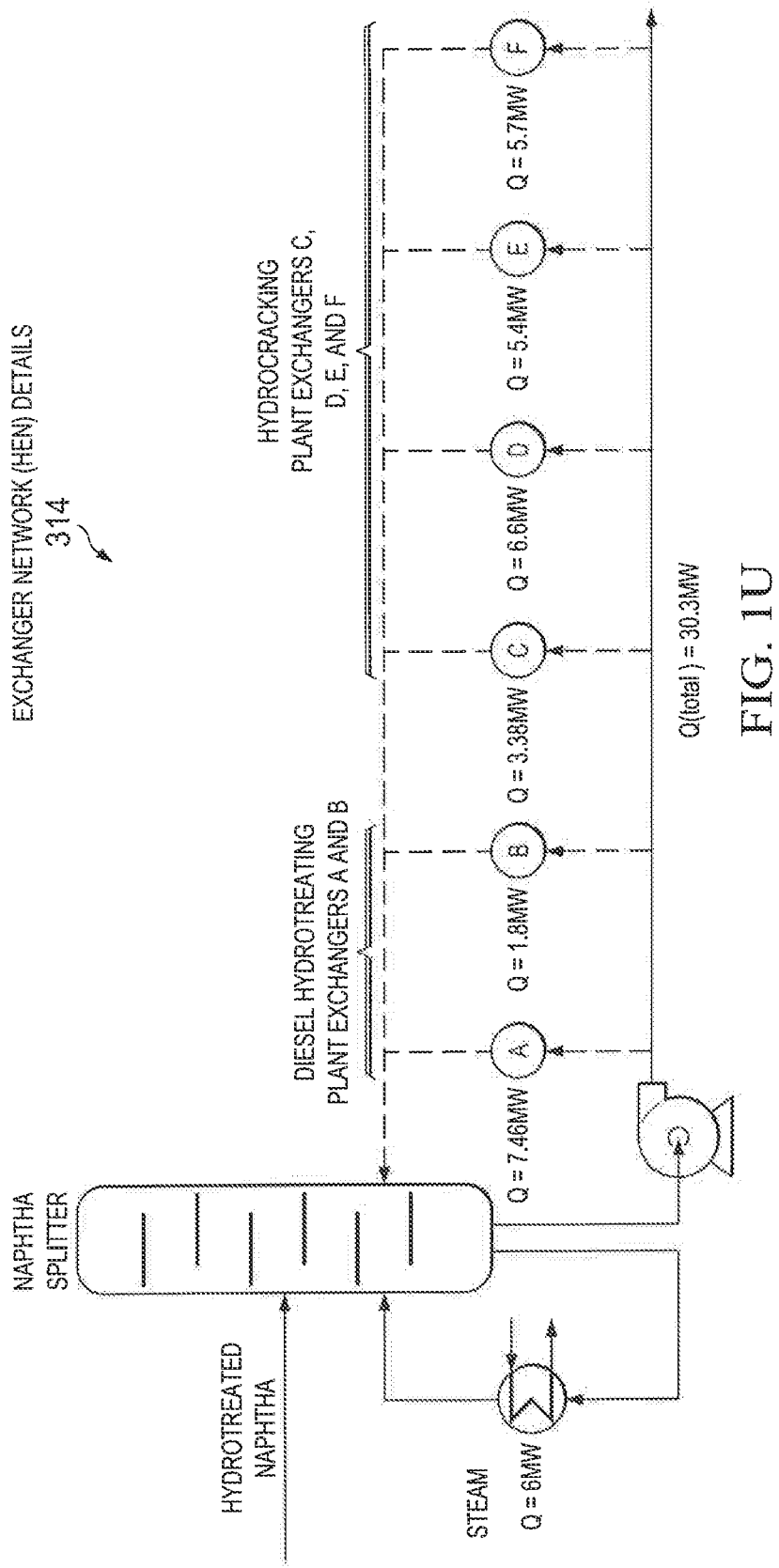

Buffer fluid is flowed to the natural gas steam reforming hydrogen plant 308. As shown in FIG. 1R, a seventh buffer fluid stream is heated using a low temperature shift (LTS) converter product stream in a seventh heat exchanger with a thermal duty that can range between about 5 MW and 15 MW (for example, 7.7 MW). The transfer of heat from this process stream into the buffer fluid captures heat that would have otherwise been discharged to the environment. The LTS converter product stream is returned to the natural gas steam reforming hydrogen plant 308 for further processing.

Buffer fluid is flowed to the diesel hydro-treating plant 300. As shown in FIG. 1S, an eighth buffer fluid stream is heated using a diesel stripper overhead stream in an eighth heat exchanger with a thermal duty that can range between about 5 MW and 15 MW (for example, 10.5 MW). The eighth heat exchanger is coupled in series with and is downstream of the A heat exchanger relative to the flow of the diesel stripper overhead stream. Also, as shown in FIG. 1S, a ninth buffer fluid stream is heated using a diesel stripper bottoms stream in a ninth heat exchanger with a thermal duty that can range between about 15 MW and 25 MW (for example, 18.4 MW). The ninth heat exchanger is coupled in series with and is downstream of the B heat exchanger relative to the flow of the diesel stripper bottoms. The transfer of heat from these process streams into the buffer fluid captures heat that would have otherwise been discharged to the environment. The diesel stripper overheads stream is returned to the diesel hydro-treating plant 300 for further processing. The first, second, third, fourth, fifth, sixth, seventh, eighth and ninth heat exchangers are coupled in parallel to each other relative to the flow of buffer fluid stream.

In some implementations, the diesel stripper overheads stream can be flowed in series through the different plants in a different order. For example, the diesel products stream can be flowed first to the eighth heat exchanger to heat the buffer fluid and then to heat exchanger A to heat one of the naphtha hydrotreating plant 314 naphtha splitter bottoms streams.

The first, second, third, fourth, fifth, sixth, seventh, eighth, and ninth heated buffer fluid streams are combined into a combined heated buffer fluid in a collection header. The combined heated buffer fluid from the collection header (or in some embodiments, a heated or insulated buffer fluid tank or storage unit that can hold heated collected buffer fluid for a period before use) can be flowed to the sour water stripper plant 310, the sulfur recovery plant 302, the amine regeneration plant 306 and the gas separation plant 304.

Figure 1V:
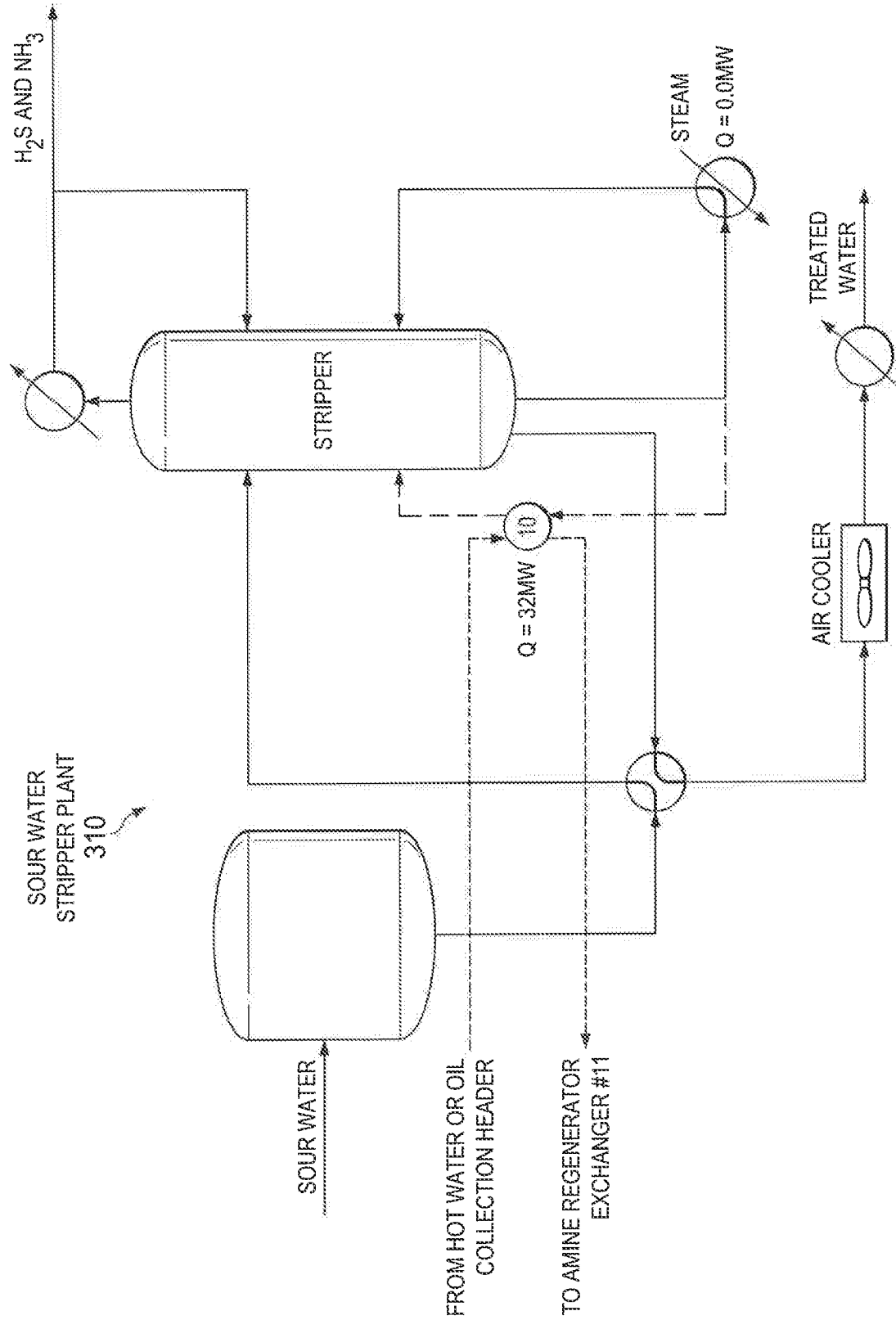

FIG. 1V shows the sour water stripper plant 310 in a crude oil refining facility. In an embodiment, the combined heated buffer fluid is flowed to the sour water stripper plant 310. The sour water stripper bottoms is heated using the combined heated buffer fluid in a tenth heat exchanger with a thermal load that can range between about 25 MW to 35 MW (for example, 32 MW). The tenth heat exchanger is coupled in series with and is downstream of the set of first, second, third, fourth, fifth, sixth, seventh, eighth, and ninth heat exchangers relative to the flow of the combined heated buffer fluid. As shown in FIG. 1V, the steam heat input for the sour water stripper can be 0 MW because the alternative flow paths disclosed in this configuration may satisfy the entire heat load for the operation of the column. In an alternative embodiment, the steam heat input for the sour water stripper can be reduced because the alternative flow paths disclosed in this configuration may partially satisfy the heat load for the operation of the column.

Figure 1W:
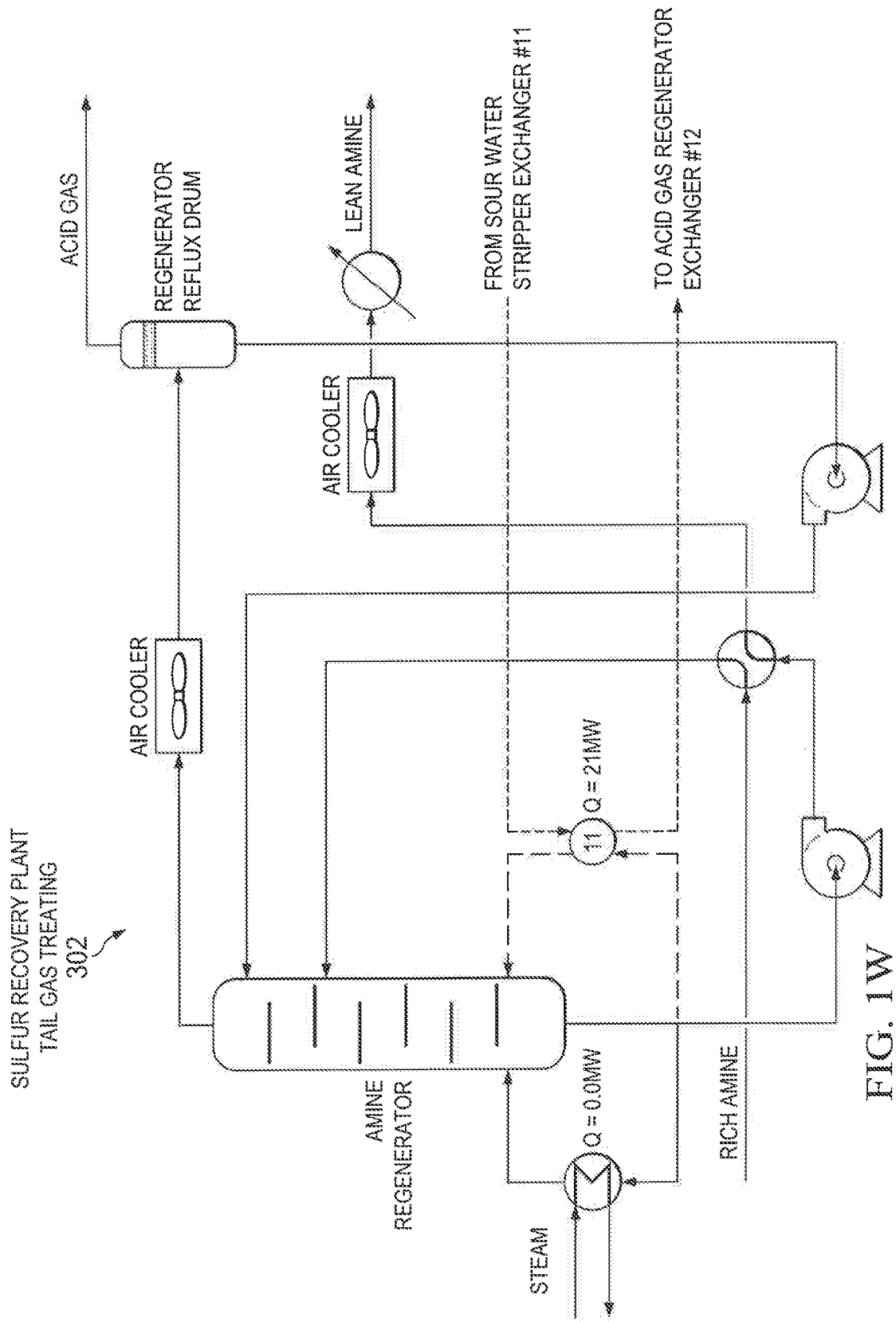

FIG. 1W shows the sour water stripper plant 310 in a crude oil refining facility. The buffer fluid exiting the tenth heat exchanger is flowed to the sulfur recovery plant 302. The amine regenerator bottoms stream is heated using the combined heated buffer fluid in an eleventh heat exchanger, which has a thermal duty that can range between about 15 MW and 25 MW (for example, 21 MW). The eleventh heat exchanger is coupled in series with and is downstream of the set of first, second, third, fourth, fifth, sixth, seventh, eighth, and ninth heat exchangers relative to the flow of the combined heated buffer fluid. As shown in FIG. 1W, the steam heat input for the amine regenerator can be 0 MW because the alternative flow paths disclosed in this configuration may satisfy the entire heat load for the operation of the column. In an alternative embodiment, the steam heat input for the amine regenerator can be reduced because the alternative flow paths disclosed in this configuration may partially satisfy the heat load for the operation of the column. The combined heated buffer fluid is flowed to the amine regeneration plant separation section 306.

Figure 1X:
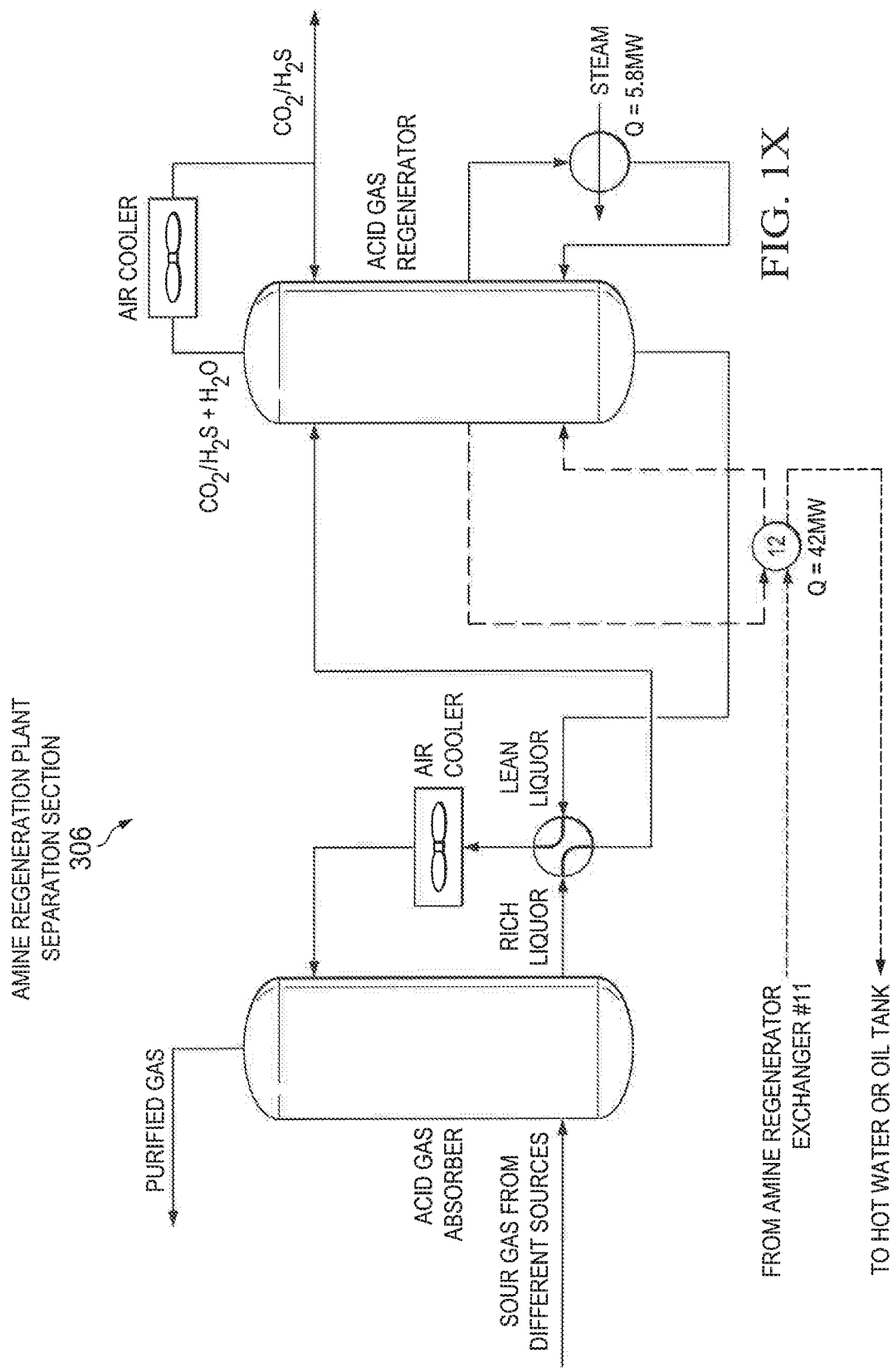

FIG. 1X shows the amine regeneration plant 306 in a crude oil refining facility. The buffer fluid exiting the eleventh heat exchanger is flowed to the amine regeneration plant 306. The acid gas regenerator bottom stream is heated using the combined heated buffer fluid in a twelfth heat exchanger, which has a thermal duty that can range between about 45 MW and 55 MW (for example, 48 MW). The twelfth heat exchanger is coupled in series with and is downstream of the set of first, second, third, fourth, fifth, sixth, seventh, eighth, and ninth heat exchangers relative to the flow of the combined heated buffer fluid. As shown in FIG. 1X, the steam heat input for the acid gas regenerator can be 0 MW because the alternative flow path disclosed in this configuration may satisfy the entire heat load for the operation of the column. In an alternative embodiment, the steam heat input for the acid gas regenerator can be reduced because the alternative flow path disclosed in this configuration may partially satisfy the heat load for the operation of the column.

The combined buffer fluid exiting the twelfth heat exchanger is flowed to a hot water or oil tank for recirculation through the heat exchangers. In this manner, the tenth heat exchanger, the eleventh heat exchanger and the twelfth heat exchanger are fluidically coupled to each other in series.

In some implementations, the heated buffer fluid can be flowed in series through different plants. For example, the heated buffer fluid can be flowed first to the sulfur recovery plant, then to the sour water stripper plant, then to the amine regeneration plant. The heated buffer fluid exiting the final heat exchanger(s) in the series can be flowed to a buffer fluid tank. The buffer fluid from the buffer fluid tank can then be flowed to the different plants to restart the waste heat recovery and reuse cycle.

Figure 1Y:
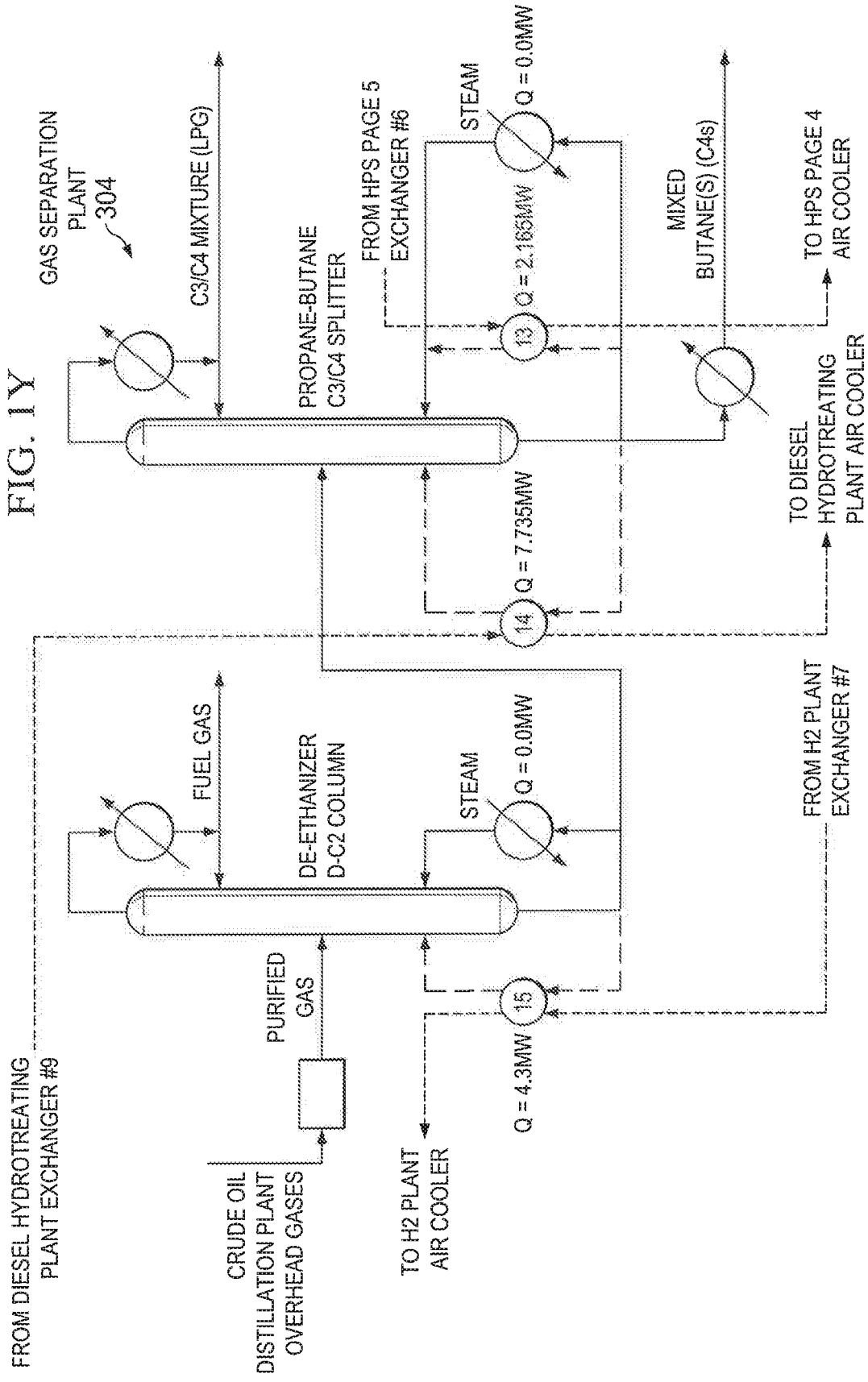

In some implementations, a gas separation plant can be heated directly by the hydrocracking plant, the diesel hydrotreating plant and the natural gas steam reforming hydrogen plant. FIG. 1Y shows a gas separations plant 304 in a crude oil refining facility. The C3/C4 splitter bottoms stream can be flowed into the plant as a single stream and split into multiple streams or it can be flowed into the plant as multiple streams. The C3/C4 splitter bottoms stream is split into a first and a second stream. A first C3/C4 splitter bottoms stream is directly heated using the kerosene product stream in a thirteenth heat exchanger with a thermal duty that can range between about 1 MW and 10 MW (for example, 2.165 MW). The thirteenth heat exchanger is coupled in series with and is downstream of the sixth and the E heat exchangers relative to the flow of the kerosene product stream. Also, a second C3/C4 splitter bottoms stream is heated directly using the diesel stripper bottoms in a fourteenth heat exchanger, which has a thermal load that can range between about 1 MW and 10 MW (for example, 7.735 MW). The fourteenth heat exchanger is coupled in series with and is downstream of the ninth and the B heat exchangers relative to the flow of the diesel stripper bottoms. The transfer of heat directly to another process stream captures heat that would have otherwise been discharged to the environment. The kerosene product stream is returned to the hydrocracking plant 312 for further processing. The diesel stripper bottoms stream is returned to the diesel hydro-treating plant 300 for further processing.

In some implementations, the kerosene product stream can be flowed in series through the different plants in a different order. For example, the kerosene product stream can be flowed first to the sixth heat exchanger to heat the buffer fluid, then to heat exchanger E to heat one of the naphtha hydrotreating plant 314 naphtha splitter bottoms streams, and then to the thirteenth heat exchanger to heat one of the C3/C4 splitter bottoms streams. As well, the diesel stripper bottoms stream can be flowed in series through the different plants in a different order. For example, the diesel stripper bottoms stream can be flowed first to the ninth heat exchanger to heat the buffer fluid, then to heat exchanger B to heat one of the naphtha hydrotreating plant 314 naphtha splitter bottoms streams, and then to the fourteenth heat exchanger to heat one of the C3/C4 splitter bottoms streams.

As shown in FIG. 1Y, the steam heat input for the C3/C4 splitter can be 0 MW because the alternative flow path disclosed in this configuration may satisfy the entire heat load for the operation of the column. In an alternative embodiment, the steam heat input for the C3/C4 splitter can be reduced because the alternative flow path disclosed in this configuration may partially satisfy the heat load for the operation of the column.

In some implementations, a de-ethanizer bottom stream can be heated directly using the LTS converter product stream in a fifteenth heat exchanger, which has a thermal duty that can range between about 1 MW and 10 MW (for example, 4 MW). The fifteenth heat exchanger is coupled in series with and downstream of the seventh heat exchanger in regards to LTS converter product stream. The LTS converter product stream is returned to the natural gas steam reforming hydrogen plant 308 for further processing.

In some implementations, the LTS converter product stream can be flowed in series through the different plants in a different order. For example, the LTS converter product stream can be flowed first to the fifteenth heat exchanger to heat the de-ethanizer bottoms stream and then to the seventh heat exchanger to heat the buffer fluid.

As shown in FIG. 1Y, the steam heat input for the de-ethanizer column can be 0 MW because the alternative flow paths disclosed in this configuration may satisfy the entire heat load for the operation of the column. In an alternative embodiment, the steam heat input for the de-ethanizer column can be reduced because the alternative flow paths disclosed in this configuration may partially satisfy the heat load for the operation of the column.

FIGS. 1M-1Y show that such recovery and reuse of waste heat directly from the hydrocracking plant, the diesel hydro-treating plant and a natural gas steam reforming hydrogen plant, and indirectly from the hydrocracking plant and the diesel hydro-treating plant, can result in decreasing or eliminating the heat energy to heat the streams in the naphtha hydro-treating plant, the sour water stripping stripper plant, the sulfur recovery plant, the amine regeneration plant, the gas separation plant or combinations of them such as by 140 MW of heat energy in a crude oil refining facility.

In summary, this disclosure describes configurations and related processing schemes of specific inter-plants waste heat recovery schemes for thermal energy consumption reduction synthesized for grassroots medium grade crude oil semi-conversion refineries to increase energy efficiency from specific portions of low grade waste heat sources. The disclosure also describes configurations and related processing schemes of specific inter-plants waste heat recovery schemes for thermal energy consumption reduction synthesized for integrated medium grade crude oil semi-conversion refineries and aromatics complex retrofit for increasing energy efficiency from specific portions of low grade waste sources.

The economics of industrial production, the limitations of global energy supply, and the realities of environmental conservation are concerns for all industries. It is believed that the world's environment has been negatively affected by global warming caused, in part, by the release of GHG into the atmosphere. Implementations of the subject matter described here can alleviate some of these concerns, and, in some cases, prevent certain refineries, which are having difficulty in reducing their GHG emissions, from having to shut down. By implementing the techniques described here, specific plants in a refinery or a refinery, as a whole, can be made more efficient and less polluting by recovery and reusing from specific portions of low grade waste heat sources.

Thus, particular implementations of the subject matter have been described. Other implementations are within the scope of the following claims.

The invention claimed is:

1. A system implemented in a crude oil refining facility comprising a plurality of oil refining plants, each oil refining plant configured to perform at least one oil refining process, each oil refining plant comprising a plurality of interconnected oil refining sub-systems, wherein a plurality of streams at respective temperatures flow between the plurality of oil refining sub-systems, the system comprising:

a hydrocracking plant stream, a low temperature shift (LTS) converter product stream and a diesel hydro-treating plant stream of a hydrocracking plant, a steam reforming hydrogen plant and a diesel hydro-treating plant, respectively, of the plurality of oil refining plants, the hydrocracking plant stream comprising at least one of a feed stream to a first reaction stage cold high pressure separator, a feed stream to a second reaction stage cold high pressure separator, a product stripper overhead stream, a diesel product stream, a kerosene pumparound stream, and a kerosene product stream;

a stream from a first oil refining plant of the plurality of oil refining plants, the first oil refining plant being different from the hydrocracking plant, the steam reforming hydrogen plant and the diesel hydro-treating plant, the first oil refining plant comprising a naphtha hydro-treating plant, a sour water stripper plant, an amine regeneration plant separation section, a sulfur recovery plant and a gas separation plant through which a gas separation plant stream comprising at least one of C2 to C4 flows; and one or more heat exchangers configured to transfer heat from one or more of the hydrocracking plant stream, the low temperature shift (LTS) converter product stream and the diesel hydro-treating plant stream to the stream from the first oil refining plant.

2. The system of claim 1, wherein the first oil refining plant comprises a naphtha hydro-treating plant, a sour water stripper plant, an amine regeneration plant separation section, a sulfur recovery plant and a gas separation plant.

3. The system claim 2, wherein the one or more heat exchangers are configured to indirectly transfer heat from one or more of the hydrocracking plant stream, the low temperature shift (LTS) converter product stream and the diesel hydro-treating plant stream to the stream from the first oil refining plant.

4. The system of claim 3, wherein the one or more heat exchangers are configured to indirectly transfer heat through a buffer fluid using one or more of the hydrocracking plant stream, the low temperature shift (LTS) converter product stream and the diesel hydro-treating plant stream.

5. The system of claim 4, wherein the buffer fluid comprises at least one of oil or water.

6. The system of claim 4, wherein the one or more heat exchangers are configured to indirectly transfer heat through the buffer fluid using one or more of the hydrocracking plant stream, the low temperature shift (LTS) converter product stream and the diesel hydro-treating plant stream, and the one or more heat exchangers comprise:

a first heat exchanger configured to heat a first buffer fluid stream using the diesel product stream in the hydrocracking plant;

a second heat exchanger configured to heat a second buffer fluid stream using the feed stream to the second reaction stage cold high pressure separator in the hydrocracking plant;

a third heat exchanger configured to heat a third buffer fluid stream using the feed stream to the first reaction stage cold high pressure separator in the hydrocracking plant;

a fourth heat exchanger configured to heat a fourth buffer fluid stream using the product stripper overhead stream in the hydrocracking plant;

a fifth heat exchanger configured to heat a fifth buffer fluid stream using the kerosene pumparound stream in the hydrocracking plant;

a sixth heat exchanger configured to heat a sixth buffer fluid stream using the kerosene product stream in the hydrocracking plant;

a seventh heat exchanger configured to heat a seventh buffer fluid stream using the low temperature shift converter product stream in the steam reforming hydrogen plant;

an eighth heat exchanger configured to heat an eight buffer fluid stream using a diesel stripper overhead stream in the diesel hydro-treating plant; and a ninth heat exchanger configured to heat a ninth buffer fluid stream using a diesel stripper bottoms stream in the diesel hydro-treating plant.

7. The system of claim 6, further comprising a combined heated buffer fluid comprising:

the heated first buffer fluid stream exiting the first heat exchanger;

the heated second buffer fluid stream exiting the second heat exchanger;

the heated third buffer fluid stream exiting the third heat exchanger;

the heated fourth buffer fluid stream exiting the fourth heat exchanger;

the heated fifth buffer fluid stream exiting the fifth heat exchanger;

the heated sixth buffer fluid stream exiting the sixth heat exchanger;

the heated seventh buffer fluid stream exiting the seventh heat exchanger;

the heated eight buffer fluid stream exiting the eighth heat exchanger; and the heated ninth buffer fluid stream exiting the ninth heat exchanger.

8. The system of claim 7, further comprising:

a tenth heat exchanger positioned in the naphtha hydro-treating plant, the tenth heat exchanger configured to heat a naphtha splitter bottoms stream in the naphtha hydro-treating plant using the combined heated buffer fluid;

an $11^{th}$ heat exchanger positioned in the sour water stripper plant, the $11^{th}$ heat exchanger configured to heat a sour water stripper bottoms stream in the sour water stripper plant using the combined heated buffer fluid;

a $12^{th}$ heat exchanger positioned in the sulfur recovery plant, the $12^{th}$ heat exchanger configured to heat an amine regenerator bottoms stream in the sulfur recovery plant using the combined heated buffer fluid;

a $13^{th}$ heat exchanger positioned in the amine regeneration plant separation section, the $13^{th}$ heat exchanger configured to heat an acid gas regenerator bottoms stream in the amine regeneration plant separation section using the combined heated buffer fluid; and a $14^{th}$ heat exchanger positioned in the gas separation plant, the $14^{th}$ heat exchanger configured to heat a C3/C4 splitter bottoms stream in the gas separation plant using the combined heated buffer fluid, the $14^{th}$ heat exchanger configured to heat a de-ethanizer bottoms stream using the combined heated buffer fluid.

9. The system of claim 8, wherein the first heat exchanger, the second heat exchanger, the third heat exchanger, the fourth heat exchanger, the fifth heat exchanger, the sixth heat exchanger, the seventh heat exchanger, the eighth heat exchanger and the ninth heat exchanger are fluidically coupled to each other in parallel.

10. The system of claim 9, wherein the tenth heat exchanger is fluidically coupled in series with a combination of the first heat exchanger, the second heat exchanger, the third heat exchanger, the fourth heat exchanger, the fifth heat exchanger, the sixth heat exchanger, the seventh heat exchanger, the eighth heat exchanger and the ninth heat exchanger.

11. The system of claim 10, wherein the tenth heat exchanger, $11^{th}$ heat exchanger, the $12^{th}$ heat exchanger, the $13^{th}$ heat exchanger, the $14^{th}$ heat exchanger and the $15^{th}$ heat exchanger are fluidically coupled to each other in series.

12. The system of claim 10, wherein the combined heated buffer fluid from the naphtha hydro-treating plant is flowed to the sour water stripper plant, then to the sulfur recovery plant, then to the amine regeneration plant separation section, and then to the gas separation plant.

13. The system of claim 1, wherein the buffer fluid comprises at least one of oil or water, and the system further comprises:

a subset of the plurality of streams in the plurality of plants, the subset comprising a sour water stripper plant stream, a sulfur recovery plant stream, an acid gas removal stream, and a gas separation plant stream;

a first heat exchanger configured to heat a first buffer fluid stream using a hydrocracking plant diesel product stream in the hydrocracking plant;

a second heat exchanger configured to heat a second buffer fluid stream using a feed stream to a second reaction stage cold high pressure separator in the hydrocracking plant;

a third heat exchanger configured to heat a third buffer fluid stream using a feed stream to a first reaction stage cold high pressure separator in the hydrocracking plant;

a fourth heat exchanger configured to heat a fourth buffer fluid stream using a product stripper overhead stream in the hydrocracking plant;

a fifth heat exchanger configured to heat a fifth buffer fluid stream using a kerosene pumparound stream in the hydrocracking plant;

a sixth heat exchanger configured to heat a sixth buffer fluid stream using a kerosene product stream in the hydrocracking plant;

a seventh heat exchanger configured to heat a seventh buffer fluid stream using a low temperature shift converter product stream in the steam reforming hydrogen plant;

an eighth heat exchanger configured to heat an eight buffer fluid stream using a diesel stripper overhead stream in the diesel hydro-treating plant; and a ninth heat exchanger configured to heat a ninth buffer fluid stream using a diesel stripper bottoms stream in the diesel hydro-treating plant.

14. The system claim 13, further comprising a combined heated buffer fluid comprising:

the heated first buffer fluid stream exiting the first heat exchanger;

the heated second buffer fluid stream exiting the second heat exchanger;

the heated third buffer fluid stream exiting the third heat exchanger;

the heated fourth buffer fluid stream exiting the fourth heat exchanger;

the heated fifth buffer fluid stream exiting the fifth heat exchanger;

the heated sixth buffer fluid stream exiting the sixth heat exchanger;
the heated seventh buffer fluid stream exiting the seventh heat exchanger;
the heated eight buffer fluid stream exiting the eighth heat exchanger; and
the heated ninth buffer fluid stream exiting the ninth heat exchanger.

15. The system of claim 14, further comprising:
a tenth heat exchanger positioned in the sour water stripper plant, the tenth heat exchanger configured to heat a sour water stripper stream in the sour water stripper plant using the combined heated buffer fluid;
an $11^{th}$ heat exchanger positioned in the sulfur recovery plant, the $11^{th}$ heat exchanger configured to heat a sulfur recovery plant amine regenerator bottoms stream in the sulfur recovery plant using the combined heated buffer fluid; and
a twelfth heat exchanger positioned in the amine regeneration plant separation section, the twelfth heat exchanger configured to heat an acid gas regenerator bottoms stream in the amine regeneration plant separation section using the combined heated buffer fluid.

16. The system of claim 15, wherein the combined heated buffer fluid is flowed to the sour water stripper plant, then to the sulfur recovery plant, and then to the amine regeneration plant separation section.

17. The system of claim 13, further comprising:
a first subset comprising a naphtha splitter bottoms stream in the naphtha hydro-treating plant;
heat exchanger A configured to heat a first branch of the naphtha splitter bottoms stream using a diesel hydro-treating plant stream using a diesel stripper overhead stream in the diesel hydro-treating plant;
heat exchanger B configured to heat a second branch of the naphtha splitter bottoms stream using the diesel hydro-treating plant stream using a stripper bottoms stream in the diesel hydro-treating plant;
heat exchanger C configured to heat a third branch of the naphtha splitter bottoms stream using a hydrocracking plant stream using a product stripper overhead stream in the hydrocracking plant;
heat exchanger D configured to heat a fourth branch of the naphtha splitter bottoms stream using the hydrocracking plant stream using a diesel product stream in the hydrocracking plant;
heat exchanger E configured to heat a fifth branch of the naphtha splitter bottoms stream using the hydrocracking plant stream using a kerosene product stream in the hydrocracking plant;
heat exchanger F configured to heat a sixth branch of the naphtha splitter bottoms stream using the hydrocracking plant stream using a kerosene pumparound stream in the hydrocracking plant stream; and
a combined heated naphtha splitter bottoms stream comprising the heated first branch, the heated second branch, the heated third branch, the heated fourth branch, the heated fifth branch, and the heated sixth branch.

18. The system of claim 17, wherein the heat exchanger A, the heat exchanger B, the heat exchanger C, the heat exchanger D, the heat exchanger E and the heat exchanger F are fluidically coupled to each other in parallel.

19. The system of claim 17, wherein the first heat exchanger is fluidically coupled in series with the heat exchanger D, wherein the fourth heat exchanger is fluidically coupled in series with the heat exchanger C, wherein the fifth heat exchanger is fluidically coupled in series with the heat exchanger F, wherein the sixth heat exchanger is fluidically coupled in series with the heat exchanger E, wherein the eighth heat exchanger is coupled in series with the heat exchanger A, wherein the ninth heat exchanger is fluidically coupled in series with the heat exchanger B.

20. The system of claim 17, wherein the first heat exchanger, the second heat exchanger, the third heat exchanger, the fourth heat exchanger, the fifth heat exchanger, the sixth heat exchanger, the seventh heat exchanger, the eighth heat exchanger and the ninth heat exchanger are fluidically coupled to each other in parallel.

21. The system of claim 20, wherein the hydrocracking plant stream used to heat the fifth branch of the naphtha splitter bottom stream in heat exchanger E comprises a kerosene product stream, and wherein the system further comprises:
a $13^{th}$ heat exchanger positioned in the gas separation plant, the $13^{th}$ heat exchanger configured to heat a first branch of a C3/C4 splitter bottoms stream in the gas separation plant using the kerosene product stream exiting heat exchanger E;
a $14^{th}$ heat exchanger positioned in the gas separation plant, the $14^{th}$ heat exchanger configured to heat a second branch of a C3/C4 splitter bottoms stream in the gas separation plant using the diesel hydro-treating plant stream exiting heat exchanger B; and
a $15^{th}$ heat exchanger positioned in the gas separation plant, the $15^{th}$ heat exchanger configured to heat a de-ethanizer bottoms stream using the low temperature shift converter product stream in the steam reforming hydrogen plant exiting the seventh heat exchanger.

22. The system of claim 21, wherein the tenth heat exchanger is fluidically coupled in series with a combination of the first heat exchanger, the second heat exchanger, the third heat exchanger, the fourth heat exchanger, the fifth heat exchanger, the sixth heat exchanger, the seventh heat exchanger, the eighth heat exchanger and the ninth heat exchanger.

23. The system of claim 22, wherein the tenth heat exchanger, the $11^{th}$ heat exchanger, the $12^{th}$ heat exchanger, the $13^{th}$ heat exchanger, and the $14^{th}$ heat exchanger are fluidically coupled to each other in series.

24. The system of claim 23, wherein the seventh heat exchanger and the $15^{th}$ heat exchanger are fluidically coupled to each other in series.

25. The system of claim 1, wherein the system comprises a flow control system.

* * * * *

UNITED STATES PATENT AND TRADEMARK OFFICE
CERTIFICATE OF CORRECTION

PATENT NO. : 10,767,932 B2  
APPLICATION NO. : 16/180828  
DATED : September 8, 2020  
INVENTOR(S) : Noureldin et al.

Page 1 of 1

It is certified that error appears in the above-identified patent and that said Letters Patent is hereby corrected as shown below:

In the Claims

Column 18, Line 35 (approx.), Claim 3, after "system" insert -- of --.

Column 20, Line 11, Claim 11, before "11$^{th}$" insert -- the --.

Column 20, Line 56, Claim 14, after "system" insert -- of --.

Signed and Sealed this  
Twenty-second Day of December, 2020

Andrei Iancu  
*Director of the United States Patent and Trademark Office*